United States Patent

Bernstein et al.

Patent Number: 5,731,309
Date of Patent: Mar. 24, 1998

[54] SUBSTITUTED HETEROALKYLENEAMINE NEUROKININ ANTAGONISTS

[75] Inventors: Peter R. Bernstein, Wallingford, Pa.; Scott C. Miller, Hamden, Conn.

[73] Assignee: Zeneca Limited, London, United Kingdom

[21] Appl. No.: 547,515

[22] Filed: Oct. 24, 1995

[30] Foreign Application Priority Data

Oct. 27, 1994 [GB] United Kingdom .................. 9421709

[51] Int. Cl.$^6$ .................. C07D 403/02; C07D 401/02; A61K 31/535; A61K 31/54

[52] U.S. Cl. .................. 514/227.8; 514/235.5; 514/235.8; 514/252; 514/255; 514/315; 514/316; 514/318; 514/320; 514/329; 514/341; 514/342; 514/343; 544/58.1; 544/59; 544/162; 544/358; 544/360; 544/382; 544/386; 546/193; 546/194; 546/195; 546/196; 546/197; 546/198; 546/199; 546/200

[58] Field of Search .................. 544/295, 58.1, 544/59, 162, 358, 360, 382, 386; 514/227.8, 235.5, 235.8, 252, 255, 315, 316, 318, 320, 329, 341, 342, 343; 546/193, 194, 195, 196, 197, 198, 199, 200

[56] References Cited

FOREIGN PATENT DOCUMENTS

| 428434 | 5/1991 | European Pat. Off. . |
| 474561 | 3/1992 | European Pat. Off. . |
| 515240 | 11/1992 | European Pat. Off. . |
| 559538 | 9/1993 | European Pat. Off. . |
| 591040 | 4/1994 | European Pat. Off. . |

OTHER PUBLICATIONS

Edmonds–Alt et al., Bioorg. Med. Chem. Lett, 3(5) 425–430, 1993.

*Primary Examiner*—Matthew V. Grumbling
*Attorney, Agent, or Firm*—Robert J. Harris; Paul R. Darkes

[57] ABSTRACT

Compounds of formula I

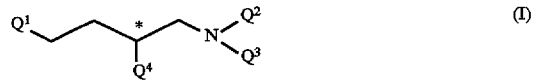

wherein $Q^1$, $Q^2$, $Q^3$, and $Q^4$ have any of the meanings given in the specification, their N-oxides, and their pharmaceutically acceptable salts are nonpeptide antagonists of SP and NKA are useful for the treatment of asthma, etc. Also disclosed are pharmaceutical compositions, processes for preparing the compounds of formula I and intermediates.

10 Claims, No Drawings

SUBSTITUTED HETEROALKYLENEAMINE NEUROKININ ANTAGONISTS

This invention concerns novel substituted 1,4-diaminobutane derivatives which antagonize the pharmacological actions of the endogenous neuropeptide tachykinins known as neurokinins, particularly at the neurokinin 1 (NK1) and the neurokinin 2 (NK2) receptors. The novel 1,4-diaminobutane derivatives are useful whenever such antagonism is desired. Thus, such compounds may be of value in the treatment of those diseases in which the NK1 and/or NK2 receptor is implicated, for example, in the treatment of asthma and related conditions. The invention also provides pharmaceutical compositions containing the novel 1,4-diaminobutane derivatives for use in such treatment, methods for their use, and processes and intermediates for the manufacture of the novel 1,4-diaminobutane derivatives.

The mammalian neurokinins comprise a class of peptide neurotransmitters which are found in the peripheral and central nervous systems. The three principal neurokinins are SP (SP), Neurokinin A (NKA) and Neurokinin B (NKB). There are also N-terminally extended forms of at least NKA. At least three receptor types are known for the three principal neurokinins. Based upon their relative selectivities favoring the neurokinin agonists SP, NKA and NKB, the receptors are classifed as neurokinin 1 (NK1), neurokinin 2 (NK2) and neurokinin 3 (NK3) receptors, respectively. In the periphery, SP and NKA are localized in C-afferent sensory neurons, which neurons are characterized by non-myelinated nerve endings known as C-fibers, and are released by selective depolarization of these neurons, or selective stimulation of the C-fibers. C-Fibers are located in the airway epithelium, and the tachykinins are known to cause profound effects which clearly parallel many of the symptoms observed in asthmatics. The effects of release or introduction of tachykinins in mammalian airways include bronchoconstriction, increased microvascular permeability, vasodilation, increased mucus secretion and activation of mast cells. Thus, the tachykinins are implicated in the pathophysiology and airway hyperresponsiveness observed in asthmatics; and blockade of the action of released tachykinins may be useful in the treatment of asthma and related conditions. A cyclopeptide antagonists (FK-224) selective for both NK1 and NK2 receptors has demonstrated clinical efficacy in human patients suffering from asthma and chronic bronchitis. M. Ichinose, et al., Lancet, 1992, 340, 1248. Nonpeptidic tachykinin antagonists have been reported, for example in European Patent Application, Publication Number (EPA) 428434, EPA 474561, EPA 512901, EPA 512902, EPA 515240 and EPA 559538, as well as in WO 94/10146, EPA 0625509 and EPA 0630887. We have discovered a series of non-peptidic antagonists of the NK1 and NK2 receptors, and this is the basis for our invention.

According to the invention, there is provided a Compound of the invention which is a compound of formula I (formula set out hereinbelow following the Examples, together with other formulae denoted by Roman numerals) wherein $Q^1$ is a radical selected from the group of radicals of formulae Ia, Ib, Ic, Id, Ie, If, Ig, Ih, Ij and Ik wherein for a radical of formula Ia, $Z^a$ is nitrogen or a group $CR^{ad}$ in which $R^{ad}$ is hydrogen or $R^{ad}$ together with $R^{ac}$ and the existing carbon to carbon bond forms a double bond; $R^{aa}$ is Ar or Het; $R^{ab}$ is hydrogen and $R^{ac}$ is hydrogen or hydroxy or $R^{ac}$ together with $R^{ad}$ and the existing carbon to carbon bond forms a double bond, or $R^{ac}$ and $R^{ad}$ together form a diradical —$(CH_2)_j$— in which j is an integer from 1 to 5; or $R^{ab}$ and $R^{ac}$ together form a diradical —$(CH_2)_k$— in which k is an integer from 2 to 6, or $R^{ab}$ and $R^{ac}$ together are oxo or dialkylaminoalkyloxyimino of formula =N—O—$(CH_2)_q$—$NR^{ae}R^{af}$ in which q is the integer 2 or 3 and $R^{ae}$ and $R^{af}$ are independently hydrogen or (1–4C)alkyl, or the radical $NR^{ae}R^{af}$ is pyrrolidino, piperidino or morpholino;

for a radical of formula Ib, $Z^b$ is a substituted imino group $R^{ba}N$ or $R^{ba}CH_2N$ in which $R^{ba}$ is (3–7C)cycloalkyl, Ar or Het; or $Z^b$ is a disubstituted methylene group $R^{bb}$ $(CH_2)_p$—C—$R^{bc}$ in which $R^{bb}$ is Ar or Het; p is the integer 0 or 1; and $R^{bc}$ is hydrogen, hydroxy, (1–4C)alkoxy, (1–4C)alkanoyloxy, $COOR^{bd}$ (wherein $R^{bd}$ is hydrogen or (1–3C)alkyl), cyano, $NR^{be}R^{bf}$ or $SR^{bg}$ in which $R^{be}$ and $R^{bf}$ are independently hydrogen, (1–4C)alkyl, (1–4C)hydroxyalkyl or (1–4C)alkanoyl, or the radical $NR^{be}R^{bf}$ is pyrrolidino, piperidino or morpholino; and $R^{bg}$ is hydrogen or (1–4C)alkyl; or $R^{bc}$ forms a double bond with the carbon atom to which it is bonded and with the adjacent carbon atom in the piperidine ring; or $Z^b$ is a disubstituted methylene group $R^{bh}CR^{bi}$ which forms a spirocyclic ring wherein $R^{bh}$ is phenyl which is joined by an ortho-substituent diradical $X^b$ to $R^{bi}$ in which the phenyl $R^{bh}$ may bear a further substituent selected from halo, (1–3C)alkyl, (1–3C)alkoxy, hydroxy, (1–3C)alkylthio, (1–3C)alkylsulfinyl and (1–3C)alkylsulfonyl; the diradical $X^b$ is methylene, carbonyl or sulfonyl; and $R^{bi}$ is oxy or imino of formula —$NR^{bj}$— in which $R^{bj}$ is hydrogen or (1–3C)alkyl;

for a radical of formula Ic, $R^{ca}$ is Ar or Het; and $Z^c$ is oxo, thio, sulfinyl, sulfonyl or imino of formula —$NR^{cb}$— in which $R^{cb}$ is (1–3C)alkyl or $R^{cc}R^{cd}N$—$(CH_2)_q$— in which q is the integer 2 or 3 and in which $R^{cc}$ and $R^{cd}$ are independently hydrogen or (1–3C)alkyl or the radical $R^{cc}R^{cd}N$ is pyrrolidino, piperidino or morpholino;

for a radical of formula Id, $R^{da}$ is 1, 2 or 3;

for a radical of formula Ie, $J^e$ is oxygen, sulfur or $NR^{ea}$ in which $R^{ea}$ is hydrogen or (1–3C)alkyl; $R^{eb}$ is hydrogen, (1–6C)alkyl which may bear a hydroxy substituent and/or one to three fluoro substituents, (3–6C)alkenyl (in which a vinyl carbon is not bound to nitrogen), 2-hydroxyethyl, (3–7C)cyloalkyl, Ar or Het; $R^{ec}$ is hydrogen, (1–6C)alkyl which may bear a hydroxy substituent and/or one to three fluoro substituents, (3–6C)cycloalkyl, (1–5C)alkoxy (only when $J^e$ is oxygen), (3–6C)cycloalkoxy (only when $J^e$ is oxygen), or an amino group of formula $NR^{ed}R^{ee}$ containing zero to seven carbon atoms in which each of $R^{ed}$ and $R^{ee}$ is independently hydrogen, (1–5C)alkyl or (3–6C)cycloalkyl, or the radical $NR^{ed}R^{ee}$ is pyrrolidino, piperidino, morpholino, thiomorpholino (or its S-oxide) or piperazinyl (which piperazinyl group may bear a (1–3C)alkyl substituent at the 4-position);

for a radical of formula If, $J^f$ is oxygen, sulfur or $NR^{fa}$ in which $R^{fa}$ is hydrogen or (1–3C)alkyl; $L^f$ is a divalent hydrocarbon group in which the 1-position is bound to the carbon bearing the group $J^f$, the divalent group $L^f$ being selected from trimethylene, cis-propenylene, tetramethylene, cis-butenylene, cis-but-3-enylene, cis,cis-butadienylene, pentamethylene and cis-pentenylene which divalent group $L^f$ itself may bear one or two methyl substituents;

for a radical of formula Ig, $Z^g$ is (1–8C)alkyl or (3–8C)cycloalkyl which may bear one or more substituents selected from the group consisting of halo, (3–6C)cycloalkyl, cyano, nitro, hydroxy, (1–4C) alkoxy, (1–5C)alkanoyloxy, aroyl, heteroaroyl, oxo, imino (which may bear a (1–6C)alkyl, (3–6C) cycloalkyl, (1–5C)alkanoyl or aroyl substituent), hydroxyimino (which hydroxyimino may bear a (1–4C)alkyl or a phenyl substituent on the oxygen), an amino group of formula $NR^{ga}R^{gb}$, an amino group of formula $NR^{gc}R^{gd}$, an amidino group of formula $C(=NR^{gg})NR^{ge}R^{gf}$, and a carbamoyl group of formula $CON(OR^{gh})R^{gi}$, but excluding any radical wherein a hydroxy and an oxo substituent together form a carboxy group, wherein an amino group of formula $NR^{ga}R^{gb}$ contains zero to seven carbon atoms and each of $R^{ga}$ and $R^{gb}$ is independently hydrogen, (1–5C)alkyl or (3–6C)cycloalkyl, or the radical $NR^{ga}R^{gb}$ is pyrrolidino, piperidino, morpholino, thiomorpholino (or its S-oxide) or piperazinyl (which piperazinyl may bear a (1–3C)alkyl substituent group at the 4-position); and wherein $R^{gc}$ is hydrogen or (1–3C)alkyl and $R^{gd}$ is (1–5C) alkanoyl, aroyl or heteroaroyl; or $R^{gd}$ is a group of formula $C(=J^g)NR^{ge}R^{gf}$ in which $J^g$ is oxygen, sulfur, $NR^{gg}$ or $CHR^{gj}$; and wherein the amino group $NR^{ge}R^{gf}$ contains zero to seven carbon atoms and each of $R^{ge}$ and $R^{gf}$ is independently hydrogen, (1–5C)alkyl or (3–6C)cycloalkyl, or the radical $NR^{ge}R^{gf}$ is pyrrolidino, piperidino, morpholino, thiomorpholino (or its S-oxide) or piperazinyl (which piperazinyl may bear a (1–3C)alkyl substituent at the 4-position) or $R^{ge}$ is hydrogen or (1–4C)alkyl and $R^{gf}$ together with $R^{gg}$ forms an ethylene or trimethylene group; $R^{gg}$ is hydrogen, (1–4C)alkyl or together with $R^{gf}$ forms an ethylene or trimethylene group; $R^{gj}$ is cyano, nitro or $SO_2R^{gk}$ and $R^{gk}$ is (1–4C)alkyl or phenyl; $R^{gh}$ and $R^{gi}$ are independently (1–3C)alkyl; and in which a cyclic group which is a substituent on $Z^g$ or formed by substitution on $Z^g$ may bear one or more (1–3C)alkyl groups on carbon as further substituents; and in which any aryl or heteroaryl group which is a part of the group $Z^g$ may bear one or more halo, (1–4C)alkyl, (1–4C) alkoxy, cyano, trifluoromethyl or nitro substituents;

for a radical of formula Ih, $G^h$ denotes a single bond, a double bond or a divalent hydrocarbon radical; $J^h$ denotes a radical joined to the ring by a single bond if $G^h$ denotes a double bond or, otherwise, a radical joined by a double bond; $M^h$ denotes a heteroatom, a substituted heteroatom, or a single bond; and $L^h$ denotes a hydrocarbon radical in which the 1-position is attached to $M^h$; wherein the values of $G^h$, $J^h$, $M^h$ and $L^h$ are selected from (a) $G^h$ is a single bond; $J^h$ is oxo or thioxo; $M^h$ is oxy, thio or $NR^{ha}$; and $L^h$ is $L^{ha}$;

(b) $G^h$ is a single bond; $J^h$ is $NR^{hb}$; $M^h$ is $NR^{ha}$; and $L^h$ is $L^{ha}$;

(c) $G^h$ is a double bond, $J^h$ is $OR^{ha}$, $SR^{ha}$ or $NR^{hc}R^{hd}$; $M^h$ is nitrogen; and $L^h$ is $L^{ha}$;

(d) $G^h$ is methylene which may bear one or two methyl substituents; $J^h$ is oxo, thioxo or $NR^{he}$; $M^h$ is oxy, thio, sulfinyl, sulfonyl or $NR^{ha}$; and $L^h$ is $L^{hb}$;

(e) $G^h$ is a single bond; $J^h$ is oxo, thioxo or $NR^{he}$; $M^h$ is nitrogen; and $L^h$ is $L^{hc}$;

(f) $G^h$ is methine, which may bear a (1–3C)alkyl substituent; $J^h$ is oxo, thioxo or $NR^{he}$; $M^h$ is nitrogen; and $L^h$ is $L^{hd}$;

(g) $G^h$ is cis-vinylene, which may bear one or two methyl substituents; $J^h$ is oxo, thioxo, or $NR^{he}$; $M^h$ is nitrogen; and $L^h$ is $L^{he}$; and (h) $G^h$ is a single bond; $J^h$ is oxo or thioxo; $M^h$ is a single bond; and $L^h$ is $L^{hf}$; wherein $R^{ha}$ is hydrogen or (1–3C)alkyl; $R^{hb}$ is hydrogen, (1–3C) alkyl, cyano, (1–3C)alkylsulfonyl or nitro; $R^{hc}$ and $R^{hd}$ are independently hydrogen or (1–3C)alkyl or the radical $NR^{hc}R^{hd}$ is pyrrolidino, piperidino, morpholino, thiomorpholino (or its S-oxide) or piperazinyl (which piperazinyl may bear a (1–3C)alkyl substituent at the 4-position); $R^{he}$ is hydrogen or (1–3C)alkyl; $L^{ha}$ is ethylene, cis-vinylene, trimethylene or tetramethylene which radical $L^{ha}$ itself may bear one or two methyl substituents; $L^{hb}$ is ethylene or trimethylene which radical $L^{hb}$ itself may bear one or two methyl substituents; $L^{hc}$ is prop-2-en-1-yliden-3-yl, which radical $L^{hc}$ itself may bear one or two methyl substituents; $L^{hd}$ is cis-vinylene, which radical $L^{hd}$ itself may bear one or two methyl substituents; $L^{he}$ is methine, which radical $L^{he}$ itself may bear a (1–3C)alkyl substituent; and $L^{hf}$ is 4-oxabutan-1,4-diyl;

for a radical of formula Ij, $X^j$ is (1–6C)alkyl, $—CH_2OR^{ja}$, $—CH_2SR^{ja}$, $—CH_2S(O)_2R^{jg}$, $—CH_2S(O)_2R^{jg}$, $—COR^{ja}$, $—COOR^{ja}$, $—C(=J^{ja})NR^{jb}R^{jc}$, $—C(R^{ja})(OR^{jd})(OR^{je})$, $—CH_2N(R^{ja})C(=J^{ja})R^{jf}$, $—CH_2N(R^{ja})COOR^{jg}$ or $—CH_2N(R^{ja})C(=J^{ja})NR^{jb}R^{jc}$;

$B^j$ is a direct bond and $L^j$ is a hydrocarbon chain in which the 1-position is bound to $B^j$ and $L^j$ is selected from trimethylene, tetramethylene, cis-1-butenylene and cis, cis-butadienylene; or $B^j$ is $N(R^{jh})$ and $L^j$ is a hydrocarbon chain selected from ethylene, trimethylene and cis-vinylene; or $B^j$ is N and $L^j$ is a hydrocarbon chain in which the 1-position is bound to $B^j$ and $L^j$ is cis,cis-prop-2-en-1-ylidin-3-yl; $J^j$ and $J^{ja}$ are independently oxygen or sulfur; $R^{ja}$, $R^{jf}$ and $R^{jh}$ are independently hydrogen or (1–6C)alkyl; $R^{jb}$ and $R^{jc}$ are independently hydrogen or (1–6C)alkyl; or the radical $NR^{jb}R^{jc}$ is pyrrolidino, piperidino, morpholino, thiomorpholino (or its S-oxide) or piperazinyl (which piperazinyl may bear a (1–3C)alkyl substituent at the 4-position); $R^{jd}$ and $R^{je}$ are independently (1–3C)alkyl or together form a divalent hydrocarbon chain selected from ethylene and trimethylene; $R^{jg}$ is (1–6C)alkyl; and for a radical of formula Ik, $Z^k$ is a nitrogen linked radical of formula II wherein $E^1$, $E^2$, $E^3$ and $E^4$ form a divalent four membered chain ($—E^1=E^2-E^3=E^4—$) in which each of $E^1$, $E^2$, $E^3$ and $E^4$ is methine; or in which one or two of $E^1$, $E^2$, $E^3$ and $E^4$ is nitrogen and the remaining $E^1$, $E^2$, $E^3$ and $E^4$ are methine; and further wherein one or more of $E^1$, $E^2$, $E^3$ and $E^4$ which is methine may bear a halo, (1–3C)alkyl, hydroxy, (1–3C)alkoxy, (1–3C) alkylthio, (1–3C)alkylsulfinyl or (1–3C) alkylsulfonyl substituent; and wherein the radicals $F^k$, $G^k$, and $I^k(X^k)$ are selected from (a) $G^k$ is a direct bond, $I^k(X^k)$ is a radical having the formula $=C(Z^k)—$ and $F^k$ is a radical selected from $—CH=$ and $—N=$;

(b) $G^k$ is a direct bond, $I^k(X^k)$ is a radical having the formula $—C(=J^k)—$ and $F^k$ is a radical selected from $—N(R^{kf})—$, $—CH_2—CH_2—$, $—CH=CH—$, $—CH_2—N(R^{kf})—$ and $—CH=N—$;

(c) $G^k$ is a radical having the formula $—CH_2—$, $I^k(X^k)$ is a radical having formula $—C(=J^k)—$ and $F^k$ is selected from $—CH_2—$ and $—N(R^{kf})—$; and (d) $G^k$ is selected from —CH$_2$—, —CH$_2$—CH$_2$—, —CH=CH— and —N=CH—, $I^k(X^k)$ is a radical having the formula —C(=J$^k$)— and $F^k$ is a direct bond; wherein $J^k$ is oxygen or sulfur; $Z^k$ is —OR$^{ka}$, —SR$^{ka}$, —COR$^{ka}$, —COOR$^{ka}$, —C(=J$^{ka}$)NR$^{kb}$R$^{kc}$ or —C(R$^{ka}$)(OR$^{kd}$)(OR$^{ke}$); $J^{ka}$ is oxygen or sulfur; R$^{ka}$ and R$^{kf}$ are independently hydrogen or (1–6C)alkyl; R$^{kb}$ and R$^{kc}$ are independently hydrogen or (1–6C)alkyl; or the radical NR$^{kb}$R$^{kc}$ is pyrrolidino, piperidino, morpholino, thiomorpholino (or its S-oxide) or piperazinyl (which piperazinyl may bear a (1–3C)alkyl substituent at the 4-position); R$^{kd}$ and R$^{ke}$ are independently (1–3C)alkyl or R$^{kd}$ and R$^{ke}$ together form ethylene or trimethylene; or $Z^k$ is an imido radical selected from phthalimido, succinimido, maleimido, glutarimido, and 3-oxa-, 3-thia- and 3-azaglutarimido, in which the imido radical may bear one or more (1–3C)alkyl substituents and, in addition, the aromatic portion of the phthalimido may bear one or more halo, hydroxy or (1–3C)alkoxy substituents; and wherein for a radical Q$^1$, Ar is a phenyl radical or an ortho-fused bicyclic carbocyclic radical of nine of ten ring atoms in which at least one ring is aromatic, which radical Ar may be unsubstituted or may bear one or more substituents selected from halo, cyano, trifluoromethyl, (1–4C)alkyl, (1–4C)alkoxy, methylenedioxy, hydroxy, mercapto, —S(O)$_n$R$^{xa}$, (1–5C)alkanoyl, (1–5C)alkanoyloxy, nitro, NR$^{xb}$R$^{xc}$, NR$^{xd}$R$^{xe}$, C(=NR$^{xf}$)NR$^{xg}$R$^{xh}$, CONR$^{xb}$R$^{xc}$ and COOR$^{xj}$ wherein n is the integer 0, 1, or 2; R$^{xa}$ is (1–6C)alkyl, (3–6C)cycloalkyl or phenyl (which phenyl may bear a halo, trifluoromethyl, (1–3C)alkyl or (1–3C)alkoxy substitutent); the radical NR$^{xb}$R$^{xc}$ contains zero to seven carbons and each of R$^{xb}$ and R$^{xc}$ is independently hydrogen, (1–5C)alkyl or (3–6C)cycloalkyl, or the radical NR$^{xb}$R$^{xc}$ is pyrrolidino, piperidino, morpholino, thiomorpholine (or its S-oxide) or piperazinyl (which piperazinyl may bear a (1–3C)alkyl substituent at the 4-position); and wherein R$^{xd}$ is hydrogen or (1–4C)alkyl and R$^{xe}$ is (1–5C)alkanoyl, benzoyl; or a group of formula C(=J$^x$)NR$^{xg}$R$^{xh}$ in which J$^x$ is oxygen, sulfur, NR$^{xf}$ or CHR$^{xi}$; R$^{xf}$ is hydrogen, (1–5C)alkyl or together with R$^{xg}$ forms an ethylene or trimethylene diradical, the radical NR$^{xg}$R$^{xh}$ contains zero to 7 carbons and each of R$^{xg}$ and R$^{xh}$ is independently hydrogen, (1–5C)alkyl or (3–6C)cycloalkyl, or the radical NR$^{xg}$R$^{xh}$ is pyrrolidino, piperidino, morpholino, thiomorpholino (or its S-oxide) or piperazinyl (which piperazinyl may bear a (1–3C)alkyl substituent at the 4-position); or R$^{xg}$ together with R$^{xf}$ forms an ethylene or trimethylene diradical and R$^{xh}$ is hydrogen or (1–5C)alkyl; R$^{xi}$ is cyano, nitro, (1–5C)alkylsulfonyl or phenylsulfonyl; and R$^{xj}$ is hydrogen, (1–5C)alkyl or benzyl; and Het is a radical (or stable N-oxide thereof) attached via a ring carbon of a monocyclic aromatic ring containing five or six ring atoms consisting of carbon and one to four heteroatoms selected from oxygen, sulfur and nitrogen, or an ortho-fused bicyclic heterocycle derived therefrom by fusing a propenylene, trimethylene, tetramethylene or benz-diradical, which radical Het may be unsubstituted or may be substituted on carbon by one or more of the substituents defined above for Ar and may be substituted on nitrogen by (1–3C)alkyl;

Q$^2$ is hydrogen, (1–3C)alkyl, phenyl(1–3C)alkyl, —C(=O)R$^2$, or —C(=O)NR$^3$R$^4$, wherein a phenyl ring may bear one or two substituents independently selected from halo, trifluoromethyl, hydroxy, (1–3C)alkoxy, (1–3C)alkyl and methylenedioxy;

Q$^3$ is phenyl(1–3C)alkyl, wherein the phenyl ring may bear one or two substituents independently selected from halo, trifluoromethyl, hydroxy, (1–3C)alkoxy, (1–3C)alkyl and methylenedioxy; or Q$^2$ and Q$^3$ together with the nitrogen to which they are attached form a phthalimide group;

Q$^4$ is phenyl which may bear one or two substituents independently selected from halo, trifluoromethyl, hydroxy, (1–3C)alkoxy, (1–3C)alkyl and methylenedioxy; or Q$^4$ is thienyl, imidazolyl, benzo[b]thiophenyl or naphthyl any of which may bear a halo substituent; or Q$^4$ is biphenylyl; or Q$^4$ is carbon-linked indolyl which may bear a benzyl substituent at the 1-position;

R$^2$ is hydrogen (1–6C)alkyl, or (1–6C)alkoxy; and

R$^3$ and R$^4$ are independently hydrogen or (1–3C)alkyl;

or the N-oxide of a piperidino nitrogen in Q$^1$ indicated by Δ in formulae Ia–Ik (or of either basic piperazinyl nitrogen of Q$^1$ when Z$^a$ is nitrogen);

or a pharmaceutically acceptable salt thereof;

or a quaternary ammonium salt thereof in which the piperidino nitrogen in Q$^1$ indicated by Δ in formulae Ia–Ik (or either basic piperazinyl nitrogen of Q$^1$ when Z$^a$ is nitrogen) is a quadricovalent ammonium nitrogen wherein the fourth radical on the nitrogen R$^1$ is (1–4C) alkyl or benzyl and the associated counterion A is a pharmaceutically acceptable anion.

It will be appreciated that a compound of formula I may contains one or more asymmetically substituted carbon atoms and that such a compound may be isolated in optically active, racemic and/or diastereomeric forms. A compound may exhibit polymorphism. It is to be understood that the present invention encompasses any racemic, optically-active, diastereomeric, polymorphic or stereoisomeric form, or mixture thereof, which form possesses NK1 and NK2 antagonist properties, it being well known in the art how to prepare optically-active forms (for example, by resolution of the racemic form or by synthesis from optically-active starting materials) and how to determine the NK1 and NK2 antagonist properties by the standard tests known in the art and those described hereinafter. It may be preferred to use the compound of formula I in a form which is characterized as containing, for example, at least 95%, 98% or 99% enantiomeric excess of the form which is of the (S)-configuration at the center indicated by * in formula I.

In this specification R$^a$, R$^b$, R$^1$, R$^2$, et cetera stand for generic radicals and have no other significance. It is to be understood that generic terms such as "(1–3C)alkyl" and "(1–6C)alkyl" include both straight and branched chain alkyl radicals but references to individual alkyl radicals such as "propyl" embrace only the straight chain ("normal") radical, branched chain isomers such as "isopropyl" being referred to specifically. A similar convention applies to other generic groups, for example, alkoxy, alkanoyl, et cetera. Halo is fluoro, chloro, bromo or iodo. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five ring atoms, consisting of carbon and one to four heteroatoms selected from oxygen, sulfur and nitrogen or containing six ring atoms consisting of carbon and one or two nitrogens, as well as a radical of an ortho-fused bicyclic heterocycle of about eight to ten atoms derived therefrom, particularly a benz-derivative or one derived by fusing a propenylene, trimethylene of tetramethylene diradical thereto, as well as a stable N-oxide thereof.

Particular values are listed below for radicals, substituents and ranges for a compound of formula I as described above for illustration only and they do not exclude other defined values or other values within defined ranges for the radicals and substituents.

A particular value for Ar is phenyl which may be unsubstituted or may bear a chloro, methyl, methoxy, hydroxy or methylsulfinyl substituent. A particular value for Het is furyl, thienyl, 2-imidazolyl, 1,3,4-oxadiazol-2-yl, pyridyl or pyrimidinyl which ring may be unsubstituted or may bear a chloro, methyl, methoxy, hydroxy, methylsulfinyl, methoxycarbonyl or ethoxycarbonyl substituent. A particular value for aryl is phenyl. A particular value for heteroaryl is furyl, pyridyl or pyrimidinyl. A particular value for halo is chloro or bromo. A particular value for (1–3C)alkyl is methyl, ethyl, propyl or isopropyl; for (1–4C)alkyl is methyl, ethyl, propyl, isopropyl, butyl, isobutyl or t-butyl; for (1–5C)alkyl is methyl, ethyl, propyl, isopropyl, butyl, isobutyl, t-butyl, pentyl or isopentyl; for (1–6C)alkyl is methyl, ethyl, propyl, isopropyl, butyl, isobutyl, t-butyl, pentyl, isopentyl, hexyl or isohexyl; and for (1–8C)alkyl is methyl, ethyl, propyl, isopropyl, isopentyl, 1-ethylpropyl, hexyl, isohexyl, 1-propylbutyl, or octyl. A particular value for (3–6C) cycloalkyl is cyclopropyl, cyclopentyl or cyclohexyl; for (3–7C)cycloalkyl is cyclopropyl, cyclopentyl, cyclohexyl or cycloheptyl; and for (3–8C)cycloalkyl is cyclopropyl, cyclopentyl, cyclohexyl, cycloheptyl or cyclooctyl. A particular value for (3–6C)alkenyl is allyl, 2-butenyl or 3-methyl-2-butenyl. A particular value for (1–4C)alkanoyl is formyl, acetyl, propionyl, butyryl or isobutyryl; and for (1–5C)alkanoyl is formyl, acetyl, propionyl, butyryl, isobutyryl, valeryl, isovaleryl or pivaloyl.

A more particular value for Ar is phenyl which may be unsubstituted or may bear a methoxy, hydroxy or methylsulfinyl substituent. A more particular value for Het is pyridyl or pyrimidinyl which ring may be unsubstituted or may bear a methoxy, hydroxy or methylsulfinyl substituent. A more particular value for heteroaryl is pyridyl. A more particular value for halo is chloro. A more particular value for (1–3C)alkyl is methyl; for (1–4C)alkyl is methyl or ethyl; for (1–5C)alkyl is methyl, ethyl, propyl or isopropyl; for (1–6C)alkyl is methyl, ethyl, propyl, isopropyl, butyl, isobutyl or t-butyl; and for (1–8C)alkyl is methyl, ethyl, propyl, isopropyl, 1-ethylpropyl or 1-propylbutyl. A more particular value for (3–6C)cylcoalkyl is cyclopropyl or cyclopentyl; for (3–7C)cycloalkyl is cyclopropyl or cyclopentyl; and for (3–8C)cycloalkyl is cyclopropyl, cyclopentyl, cyclohexyl or cycloheptyl. A more particular value for (3–6C)alkenyl is allyl. A more particular value for (1–4C)alkanoyl is formyl or acetyl; and for (1–5C)alkanoyl is formyl, acetyl, propionyl, butyryl or isobutyryl.

A particular value for $Q^1$ is 4-acetamido-4-phenylpiperidino, 4-(2-methylsulfinylphenyl)piperidino, 4-(2-oxopiperidino)piperidino, or 4-(2-oxoperhydropyrimidin-1-yl)piperidino; for $Q^2$ is hydrogen, benzyl, formyl, phenethyl, N-methylaminocarbonyl, acetyl, or methyl; for $Q^3$ is benzyl, phenethyl, 3,5-bis (trifluoromethyl)benzyl, 3,5-bis(trifluoromethyl)phenethyl, 3-methoxybenzyl or 2-methoxybenzyl; and for $Q^4$ is 3,4-dichlorophenyl, or 3,4-methylenedioxyphenyl.

A more particular value for $Q^1$ is 4-acetamido-4-phenylpiperidino; and for $Q^3$ is 2-methoxybenzyl.

A particular group of compounds of formula I are compounds wherein $Q^1$ is a radical of formula Ia, Ib, Ic, Id, Ie, If, Ig, Ih, Ij or Ik.

A particular group of compounds of formula I are compounds wherein $Q^1$ is selected from the radicals of formulae Ie, If, Ig, Ih, Ij and Ik.

A particular group of compounds of formula I are compounds of formula III wherein, $Q^2$ and $Q^3$ have any of the values defined above.

A particular group of compounds of formula I are compounds wherein $Q^2$ is hydrogen or methyl.

Pharmaceutically acceptable salts of a compound of formula I include those made with a strong inorganic or organic acid which affords a physiologically acceptable anion, such as, for example, hydrochloric, sulfuric, phosphoric, methanesulfonic, or para-toluenesulfonic acid.

A compound of formula I may be made by processes which include processes known in the chemical art for the production of structurally analogous heterocyclic compounds. Such processes and intermediates for the manufacture of a compound of formula I as defined above are provided as further features of the invention and are illustrated by the following procedures in which the meanings of generic radicals are as defined above unless otherwise indicated:

(a) For a compound of formula I wherein $Q^2$ is hydrogen, (1–3C)alkyl, or phenyl(1–3C)alkyl, reductively alkylating an amine of formula IV with a suitable aldehyde. The reductive alkylation is preferably carried out under conventional reductive alkylation conditions, for example by the in situ, acid-catalyzed formation of an imminium salt followed by reduction with sodium cyanoborohydride in alcoholic solvent, as described in Examples 1 and 14, (b) For a compound of formula I wherein $Q^2$ is hydrogen, (1–3C)alkyl, or phenyl(1–3C)alkyl, alkylating an amine of formula IV with an alkylating agent of formula V in which Y is a leaving group. Typical values for a leaving group Y include, for example, iodide, bromide, methanesulfonate, p-toluenesulfonate, trifluoromethanesulfonate, and the like. The reaction may be carried out under standard conditions, for example in a suitable inert solvent, such as for example dichloromethane, chloroform, tetrahrdrofuran, toluene or diethyl ether, at a temperature in the range of –50° to 100° C., preferably in the range of 0° to 50° C.

(c) For a compound of formula I wherein $Q^2$ is —C(=O) $R^2$, by acylation of an amine of formula VI with an corresponding activated acid derivative of formula VII such as for example an acid chloride wherein X is chloro, or an acid anhydride, wherein X is $R^2C(=O)$ O—. The acylation may conveniently be carried out in an inert solvent such as for example dichloromethane, chloroform, tetrahrdrofuran, toluene or diethyl ether, at a temperature in the range of –50° to 100° C., preferably in the range of –20° to 50° C.; and may conveniently be carried out in the presence of a suitable base. Suitable conditions for the acylation of an amine of formula VI are described in Example 10.

(d) For a compound of formula I wherein $Q^2$ is formyl, by formylating a corresponding compound of formula I wherein $Q^2$ is hydrogen, using standard conditions. The formylation may conveniently be carried out in the presence of a suitable coupling reagent, such as for example 1,1'carbonyldiimidazole, in an inert solvent, such as for example tetrahydrofuran, toluene or diethyl ether, at a temperature in the range of –50° to 100° C., preferably in the range of 0° to 50° C. Suitable conditions for the formylation of an amine of formula IV are described in Example 2.

(e) For an N-oxide of a piperidino nitrogen in $Q^1$ indicated by Δ in formulae Ia–Ik (or of either basic piperazinyl nitrogen of $Q^1$ when $Z^a$ is nitrogen); oxidizing the piperidino nitrogen of a corresponding compound of formula I using a conventional procedure, such as, for example, using hydrogen peroxide in methanol, peracetic acid, 3-chloroperoxybenzoic acid in an inert solvent (such as dichloromethane) or dioxirane in acetone.

(f) For a quaternary ammonium salt of the piperidino nitrogen in $Q^1$ indicated by Δ in formulae Ia–Ik (or either basic piperazinyl nitrogen of $Q^1$ when $Z^a$ is nitrogen), alkylating the piperidino nitrogen in a corresponding compound of formula I with an alkylating agent of formula $R^1Y$ wherein Y is a leaving group.

(g) For a compound of formula I which bears a sulfinyl group, oxidizing the sulfur of a corresponding compound of formula I which bears a sulfide group using a conventional method.

(h) For a compound of formula I which bears a sulfonyl group, oxidizing a sulfide or sulfinyl group of a corresponding compound of formula I using a conventional method.

(i) For a compound of formula I which bears an aromatic hydroxy group, cleaving the ether of a corresponding compound of formula I which bears an aromatic alkoxy group using a conventional method.

It may be desired to optionally use a protecting group during all or portions of the above described processes; the protecting group then may be removed when the final compound is to be formed.

Whereafter, for any of the above procedures, when a pharmaceutically acceptable salt of a compound of formula I is required, it may be obtained by reacting the compound of formula I with an acid affording a physiologically acceptable counterion or by any other conventional procedure.

It will also be appreciated that certain of the various optional substituents in the compounds of the invention may be introduced by standard aromatic substitution reactions or generated by conventional functional group modifications either prior to or immediately following the processes above, and as such are included in the process aspect of the invention. The reagents and reaction conditions for such procedures are well known in the chemical art.

If not commercially available, the necessary starting materials for the above procedures may be made by procedures which are selected from standard techniques of organic chemistry, techniques which are analogous to the synthesis of known, structurally similar compounds and techniques which are analogous to the above described procedures or the procedures described in the Examples. The starting materials and the procedures for their preparation are additional aspects of the invention.

A convenient intermediate for the preparation of a compound of formula I is an amine of formula IV, wherein $Q^2$ is hydrogen, which can be prepared as shown in Scheme I. Alkylation of a nitrile of formula VIII with 2-tetrahydropyran-2-yloxyethyl bromide followed by reduction of the nitrile yields an amine of formula X. Hydrolysis of the acetal, followed by protection of the amine, for example by formation of a phthalimide derivative, yields an alcohol of formula XI. Oxidation of the alcohol yields an aldehyde of formula XII. Reductive coupling of an aldehyde of formula XII with an amine of formula $Q^1H$ yields an intermediate of formula XIII, which is also a compound of the invention. Deprotection of the amine yields a compound of formula IV wherein $Q^2$ is hydrogen.

Piperidines of formula $Q^1$—H can be prepared from readily available starting materials using known synthetic methods. For example, the preparation of piperidines of formula $Q^1$—H is disclosed in European Patent Application, Publication Number (EPA) 428434, EPA 474561, EPA 512901, EPA 512902, EPA 515240 and EPA 559538, as well as in WO 94/10146, EPA 0625509 and EPA 0630887. As will be clear to one skilled in the art, a variety of sequences are available for preparation of the starting materials, and the sequences leading to the starting materials and products of the invention may be altered if appropriate considerations regarding the synthetic methods and radicals present are followed.

The utility of a compound of the invention or a pharmaceutically acceptable salt thereof (hereinafter, collectively referred to as a "Compound") may be demonstrated by standard tests and clinical studies, including those disclosed in the EPA publications noted above, and those described below.

SP Receptor Binding Assay (Test A)

The ability of a Compound of the invention to antagonize the binding of SP at the NK1 receptor may be demonstrated using an assay using the human NK1 receptor expressed in Mouse Erythroleukemia (MEL) cells. The human NK1 receptor was isolated and characterized as described in: B. Hopkins, et al. "Isolation and characterization of the human lung NK1 receptor cDNA" *Biochem. Biophys. Res. Comm.*, 1991, 180, 1110–1117; and the NK1 receptor was expressed in Mouse Erythroleukemia (MEL) cells using a procedure similar to that described in Test B below.

Neurokinin A (NKA) Receptor Binding Assay (Test B)

The ability of a Compound of the invention to antagonize the binding of NKA at the NK2 receptor may be demonstrated using an assay using the human NK2 receptor expressed in Mouse Erythroleukemia (MEL) cells, as described in: Aharony, D., et al. "Isolation and Pharmacological Characterization of a Hampster Neurokinin A Receptor cDNA" *Molecular Pharmacology*, 1994, 45, 9–19. In an initial use of this assay, the $IC_{50}$ measured for the standard compound L-659,877 was found to be 30 nM versus $^3$H-NKA binding to MELM.

The selectivity of a Compound for binding at the NK1 and the NK2 receptors may be shown by determining its binding at other receptors using standard assays, for example, one using a tritiated derivative of NKB in a tissue preparation selective for NK3 receptors.

In general, the Compounds of the invention which were tested demonstrated statistically significant binding activity in Test A and Test B with a $K_i$ of 1 μM or much less typically being measured. For example, the compound of Example 3 demonstrated a Ki of 0.43 uM in Test A, and a Ki of 0.013 uM in Test B.

Rabbit Pulmonary Artery: NK1 in vitro functional assay (Test C)

The ability of a Compound of the invention to antagonize the action of the agonist, Ac-[Arg$^6$, Sar$^9$, Met(O$_2$)$^{11}$]SP(6-11) (designated ASMSP) in a pulmonary tissue may be demonstrated using a functional assay which is carried out under conditions similar to those described in: Emonds-Alt, X., et al. "In vitro and in vivo biological activities of Sr 140333, a novel potent non-peptide tachykinin NK$_1$ receptor antagonist" *Eur. J. Pharmacol.*, 1993, 250, 403–413; and which is carried out as follows.

Male New Zealand white rabbits are killed by lethal injection (Nembutal, 60 mg/kg into a cannulated ear vein). Heparin, 0.0025 ml/kg of a 1000 U/ml solution, is injected into the ear vein prior to nembutal in order to decrease blood coagulation. The left and right branches of the pulmonary artery are isolated from the rest of the lung tissue and cut in half to provide four ring segments from each animal. The segments, with intact endothelium, are suspended between stainless steel stirrups and placed in water-jacketed (37.0° C.) tissue baths containing physiological salt solution of the following composition (mM): NaCl, 119.0; KCl 4.6; $CaCl_2$, 1.8; $MgCl_2$, 0.5; $NaH_2PO_4$, 1.0; $NaHCO_3$, 25.0; glucose 11.0; indomethacin 0.005 (to inhibit cyclooxygenase); and dl-propranolol, 0.001 (to inhibit β-adrenergic receptors); gassed continuously with 95% $O_2$–5% $CO_2$. Initial tension placed on each tissue is 2 grams, which is maintained throughout a 0.5 hour equilibration period. Changes in tension are measured on a Grass polygraph via Grass FT-03 force transducers.

Thiorphan, $1\times10^{-6}$M (to inhibit E.C.3.4.24.11), and a selective NK2 antagonist (to inhibit $NK_2$ receptors) such as for example, an antagonist described in WO 94/148,184, EPA 0625509, EPA 0630887, or the antgonist SR48968 ($3\times10^{-8}$M), are added to the tissue baths along with the test compound or its vehicle 90 minutes before the $NK_1$ receptor agonist, Ac-[$Arg^6$, $Sar^9$, $Met(O_2)^{11}$]Sp(6-11) (designated ASMSP). Phenylephrine, $3\times10^{-6}$M, is added in order to induce tone in the tissue. One hour after introducing phenylephrine, cumulative concentration response effects of ASMSP are obtained and papaverine, $1\times10^{-3}$M, is added at the end of each experiment to determine the maximum magnitude of relaxation (defined as 100%).

Potencies of the compounds are determined by calculating the apparent dissociation constants ($K_B$) for each concentration tested using the standard equation:

$$K_B=[\text{antagonist}]/(\text{dose ratio}-1)$$

where dose ratio=antilog[(agonist-log molar $EC_{50}$ without compound)−(agonist-log molar $EC_{50}$ with compound)]. The $K_B$ values are converted to the negative logarithms and expressed as −log molar $K_B$ (i.e. $pK_B$). The potency of the agonist is determined at 50% of its own maximum relaxation in each curve. The $EC_{50}$ values are converted to negative logarithms and expressed as −log molar $EC_{50}$. Maximum relaxation responses to ASMSP are determined by expressing the maximum response to the agonist as a percentage of the relaxation caused by papaverine.

Guinea Pig Trachea Assay: NK2 in vitro functional assay (Test D)

The ability of a Compound of the invention to antagonize the action of the agonist, [β-Ala8]-Neurokinin A(4-10) (designated BANK), in a pulmonary tissue may be demonstrated using a functional assay in guinea pig trachea which is carried out under conditions similar to those described in: Ellis, J. L., et al., "Pharmacological examination of receptors mediating contractile responses to tachykinins in airways isolated from human, guinea pig and hamster" *J. Pharmacol. Exp. Ther.*, 1993, 267, 95–101; and which is carried out as follows.

Male guinea pigs are killed by a sharp blow to the back of the head followed by exsanguination. The trachea are removed, trimmed of excess tissue (including removal of epithelium) and cut in spiral fashion. Each longitudinally cut tracheal segment is suspended as a strip in a water-jacketed (37.5° C.) tissue bath containing a physiological salt solution of the following composition (mM): NaCl, 119; KCl 4.6; $CaCl_2$, 1.8; $MgCl_2$, 0.5; $NaH_2PO4$, 1; $NaHCO3$, 25; glucose, 11; and indomethacin, 0.005 (to inhibit cyclooxygenase); gassed continuously with 95% O2–%5 $CO_2$. Initial tension placed on each tissue is 5 g, which is maintained throughout a 0.5 hour equilibration period before addition of other drugs. Contractile responses are measured on a Grass polygraph via Grass FT-03 force transducers.

Tissues are challenged once with a single concentration of capsaicin ($1\times10^{-6}$M) and washed extensively before addition of a selective NK1 antagonist, such as for example (+)-CP96345 ($3\times10^{-7}$M) (to block NK1 receptors) and thiorphan, $1\times10^{-6}$M (to block E.C.3.4.24.11). Cumulative addition of the $NK_2$ agonist [β-Ala8]-Neurokinin A(4-10) (designated BANK) is begun 35 minutes after addition of thiorphan. Test compound is added 120 min before BANK.

Potencies of the compounds are evaluated by calculating apparent dissociation constants ($K_B$) for each concentration tested using the standard equation:

$$K_B=[\text{antagonist}]/(\text{dose ratio}-1)$$

where dose ratio=antilog[(agonist −log molar $EC_{50}$ without compound)−(agonist–log molar $EC_{50}$ with compound)]. The $K_B$ values are converted to the negative logarithms and expressed as −log molar $K_B$ (i.e. $pK_B$). The potency of BANK is determined at 50% of its own maximum response level in each curve. The $EC_{50}$ values are converted to the negative logarithms and expressed as −log molar $EC_{50}$. Maximum contractile responses to BANK are determined by expressing the maximum response to BANK as a percentage of the initial contraction caused by capasacin.

In general, the Compounds of the invention which were tested demonstrated functional activity in Tests C and D, with a pKB of 5 or greater typically being measured in each test. For Example, the compound of Example 10 demonstrated a pKB of 6.02 in Test C, and a pKB of 5.50 in Test D.

Guinea Pig Labored Abdominal Breathing (Dyspnea) Assay: $NK_1$ and $NK_2$ in vivo functional assay (Test E)

The activity of a compound as an antagonist of $NK_1$ or $NK_2$ receptors also may be demonstrated in vivo in laboratory animals, for example by adapting a routine guinea pig aerosol test described for evaluation of leukotriene antagonists in: Snyder, et al. "Conscious guinea-pig aerosol model for evaluation of peptide leukotriene antagonists" *J. Pharmacol. Meth.*, 1988, 19, 219, which is carried out as follows.

Using the clear plastic chamber described previously by Snyder et al. to secure guinea pigs for a head-only aerosol exposure to bronchoconstrictor agonists, agonist is administered by aerosol to six conscious guinea pigs simultaneously during each maneuver. The tachykinin $NK_1$-selective agonist ASMSP or the tachykinin $NK_2$-selective agonist, BANK, $3\times10^{-5}$M of either, is aerosolized from a Devilbiss Model 25 ultrasonic nebulizer into an air stream entering the chamber at a rate of 2 L/minute.

Guinea pigs (275–400 g) are fasted for approximately 16 hours prior to experimentation. Compounds to be evaluated for blockade of effects of ASMSP or BANK or their vehicle (10% PEG400 in saline) are given by p.o., i.v. or aerosol routes of administration at various times before aerosol agonist challenge. All animals are pretreated with atropine (10 mg/kg, i.p., 45 minutes pretreatment) indomethacin (10 mg/kg, i.p. 30 minutes pretreatment), propranolol (5 mg/kg, i.p., 30 minutes pretreatment), and thiorphan (1 mg/ml aerosol for 5 minutes, 15 minutes pretreatment).

Aerosol challenge with the agonist produces an initial increase in respiratory rate followed by a decrease with early signs of minor involvement of the abdominal muscles. The respiratory rate decreases further and the breathing becomes more labored with greater involvement of the abdominal muscles as exposure continues. The distinctly recognizable end point is the point where the breathing pattern of the guinea pig is consistently slow, deep, and deliberate, showing marked involvement of the abdominal muscles. Time, in seconds, from the onset of aerosol challenge to this end point is determined for each animal by using a stopwatch. The animals generally collapsed after reaching the end point and did not recover from the agonist-induced respiratory distress. Antagonists result in an increase in the time to reach the end point. Animals receive the aerosol administration of agonist for a maximum time of 780 seconds.

Differences between drug-treated groups and corresponding vehicle-treated control groups are compared using Student's t-test for unpaired observations. Results are reported as % protection values, where % protection=

[(drug time−mean control time)/(maximal aerosol time−mean control time)]×100

Clinical Studies

Clinical studies to demonstrate the efficacy of a Compound of the invention may be carried out using standard methods. For example, the ability of a Compound to prevent or treat the symptoms of asthma or asthma-like conditions may be demonstrated using a challenge of inhaled cold air or allergen and evaluation by standard pulmonary measurements such as, for example, $FEV_1$ (forced expiratory volume in one second) and FVC (forced vital capacity), analyzed by standard methods of statistical analysis.

It will be appreciated that the implications of a Compound's activity in the above described Tests is not limited to asthma, but rather, that the Tests provide evidence of general antagonism of both SP and NKA SP and NKA have been implicated in the pathology of numerous diseases including: rheumatoid arthritis, Alzheimer's disease, oedema, allergic rhinitis, inflamation pain, gastrointestinal-hypermotility, anxiety, emesis, Huntington's Disease, Psycoses, hypertension, migraine, bladder hypermotility and uticaria. Accordingly, one feature of the invention is the use of a compound of formula I or a pharmaceutically acceptable salt thereof in the treatment of a disease in a human or other mammal in need thereof in which SP or NKA is implicated and antagonism of its action is desired.

Asthma is characterized by both chronic inflammation and hyperresponsiveness of the airways. The NK1 receptor is known to mediate inflammation and mucus hypersecretion in airways; and the NK2 receptor is involved in the control of the tone of bronchial smooth muscle. Thus, agents capable of antagonizing the actions of SP and NKA, at the NK1 and NK2 receptors, respectively, are capable of reducing both the chronic inflammation and the airway hyperresponsiveness which are symptomatic of asthma. It has been suggested that an antagonist having mixed affinity for NK1 and NK2 could be therapeutically superior to a receptor selective antagonist. C. M. Maggi "Tachykinin Receptors and Airway Pathophysiology" EUR. Respir. J., 1993, 6, 735–742 at 739. Also, it has been suggested that a synergistic effect against bronchoconstriction may result from the simultaneous application of an NK1 antagonist and an NK2 antagonist. D. M. Foulon, et al. "NK1 and NK2 Receptors Mediated Tachykinin and Resiniferatoxin-induced Bronchospasm in Guinea Pigs" American Review of Respiratory Disease, 1993, 148, 915–921. Accordingly, another feature of the invention is the use of a compound of formula I or a pharmaceutically acceptable salt thereof in the treatment of asthma in a human or other mammal in need thereof.

Because of the range of effects attributable to the actions of SP and NKA, compounds which are capable of blocking their actions may also be useful as tools for further evaluating the biological actions of other neurotransmitters in the Tachykinin family. As a result, another feature of the invention is provided by the use of a compound of formula I or a salt thereof as a pharmacological standard for the development and standardization of new disease models or assays for use in developing new therapeutic agents for treating diseases in which SP or NKA are implicated or for assays for their diagnosis.

When used in the treatment of a disease, a compound of the invention is generally administered as an appropriate pharmaceutical composition which comprises a compound of formula I or a pharmaceutically acceptable salt thereof as defined hereinbefore and a pharmaceutically acceptable diluent or carrier, the composition being adapted for the particular route of administration chosen. Such a composition is provided as a further feature of the invention. It may be obtained employing conventional procedures and excipients and binders, and it may be one of a variety of dosage forms. Such forms include, for example, tablets, capsules, solutions or suspensions for oral administration; suppositories for rectal administration; sterile solutions or suspensions for administration by intravenous or intramuscular infusion or injection; aerosols or nebulizer solutions or suspensions for administration by inhalation; or powders together with pharmaceutically acceptable solid diluents such as lactose for administration by insufflation.

For oral administration a tablet or capsule containing up to 250 mg (and typically 5 to 100 mg) of a compound of formula I may conveniently be used. For administration by inhalation, a compound of formula I will be administered to humans in a daily dose range of, for example, 5 to 100 mg, in a single dose or divided into two to four daily doses. Similarly, for intravenous or intramuscular injection or infusion a sterile solution or suspension containing up to 10% w/w (and typically 0.05 to 5% w/w) of a compound of formula I may conveniently be used.

The dose of a compound of formula I to be administered will necessarily be varied according to principles well known in the art taking account of the route of administration and the severity of the condition and the size and age of the patient under treatment. However, in general, the compound of formula I will be administered to a warm-blooded animal (such as man) so that a dose in the range of, for example, 0.01 to 25 mg/kg (and usually 0.1 to 5 mg/kg) is received. It will be understood that generally equivalent amounts of a pharmaceutically acceptable salt of a compound of formula I may be used.

The invention will now be illustrated by the following non-limiting examples in which, unless stated otherwise:

(i) temperatures are given in degrees Celsius (°C.); operations were carried out at room or ambient temperature, that is, at a temperature in the range of 18°–25° C.;

(ii) organic solutions were dried over anhydrous magnesium sulfate; evaporation of solvent was carried out using a rotary evaporator under reduced pressure (600–4000 pascals; 4.5–30 mm Hg with a bath temperature of up to 60° C.;

(iii) chromatography means flash chromatography on silica gel; thin layer chromatography (TLC) was carried out on silica gel plates;

(iv) in general, the course of reactions was followed by TLC and reaction times are given for illustration only;

(v) melting points are uncorrected and (dec) indicates decomposition; the melting points given are those obtained for the materials prepared as described; polymorphism may result in isolation of materials with different melting points in some preparations;

(vi) final products had satisfactory proton nuclear magnetic resonance (NMR) spectra;

(vii) yields are given for illustration only and are not necessarily those which may be obtained by diligent process development; preparations were repeated if more material was required;

(viii) when given, NMR data is in the form of delta values for major diagnostic protons, given in parts per million (ppm) relative to tetramethylsilane (TMS) as an internal standard, determined at 300 MHz using perdeuterio dimethyl sulfoxide (DMSO-$d_6$) as solvent; conventional abbreviations for signal shape are used; for AB spectra the directly observed shifts are reported; coupling constants (J) are given in Hz; Ar designates an aromatic proton when such an assignment is made;

(ix) chemical symbols have their usual meanings; SI units and symbols are used;

(x) reduced pressures are given as absolute pressures in pascals (Pa); elevated pressures are given as gauge pressures in bars;

(xi) solvent ratios are given in volume:volume (v/v) terms;

and (xii) mass spectra (MS) were run with an electron energy of 70 electron volts in the chemical ionization (CI) mode using a direct exposure probe; where indicated ionization was effected by electron impact (EI) or fast atom bombardment (FAB); values for m/z are given; generally, only ions which indicate the parent mass are reported.

EXAMPLE 1

4-(4-Acetamido-4-phenylpiperidino)-2-(3,4-dichlorophenyl)-N-[3,5-bis(trifluoromethyl)benzyl]butylamine To a solution of 4-(4-acetamido-4-phenylpiperidino)-2-(3,4-dichlorophenyl)butylamine (0.30 g) in methanol (3 mL) was added 3,5-bis(trifluoromethyl)benzaldehyde (0.088 mL) and the mixture cooled to 0° C. To this stirred mixture was sequentially added acetic acid (0.046 mL) and a solution of sodium cyanoborohydride (0.50 g) in methanol (1 mL). The mixture was allowed to slowly warm to room temperature overnight and was diluted with dichloromethane (5 mL), water (5 mL), and hydrochloric acid (1N, 5 mL). The layers were separated, and the aqueous layer was extracted three times with dichloromethane (10 mL). The acidic aqueous layer was made basic with aqueous sodium hydroxide (1N, 5 mL) and then extracted with 5:1 dichloromethane:methanol (3×10 mL). The combined organic layers were washed (brine), dried, filtered and evaporated to afford an oil which was purified by chromatography, with dichloromethane:methanol (40:1) as eluent. Evaporation of the appropriate fractions afforded a partial hydrate of the title compound as a white solid (0.154 g); mp 66°–68° C.; NMR: 7.82 (s,3), 7.75 (s,1), 7.50 (m,2), 7.35–5.15 (m,6), 2.75 (m,1), 2.65–2.55 (m,2), 2.32–1.95 (m,6), 1.85 (s,3), 1.95–1.55 (m,6); MS: m/z=660(M+1, 100%); $R_f$=0.51 (10:1, dichloromethane:methanol). Analysis for $C_{32}H_{33}Cl_2F_6N_3O \cdot 0.25 H_2O$: Calculated: C, 57.79; H, 5.08; N, 6.32; Found: C, 57.68; H, 5.07; N, 6.30.

The intermediate 4-(4-acetamido-4-phenylpiperidino)-2-(3,4-dichlorophenyl)butylamine was prepared as follows.

a. 2-Tetrahydropyran-2-yloxyethyl bromide. To a mechanically stirred solution of dihydropyran (1000 mL) and a strong acid resin (10.0 g) in hexane (2000 mL) was added 2-bromoethanol (985 g) dropwise over a period of 1.5 hours in a cold water bath to maintain an internal temperature of 35°–40° C. After being stirred overnight at room temperature, the reaction mixture was chromatographed, with hexane as the eluent. The hexane was evaporated to give an amber liquid which was distilled through a 2 inch (5 cm) diameter vigreux column, collecting the material boiling between 75°–95° C. (3,300–4,700 Pa). This material was redistilled to give the ether as an oil (1195.5 g); bp 80°–90° C. (2666 Pa); NMR: 4.68 (m,1), 4.01 (m,1), 3.89 (m,1), 3.77 (m,1), 3.52 (m,3), 1.75–1.50 (m,6).

b. α-[2-(Tetrahydropyran-2-yloxy)ethyl]-3,4-dichlorophenylacetonitrile. To a solution of sodium hydride (218.0 g of a 55% oil suspension) in tetrahydrofuran (4 L) at 10° C. in an ice/water bath was added 3,4-dichlorophenylacetonitrile (893.0 g) in tetrahydrofuran (2 L) over a period of 45 minutes, and the resulting solution was allowed to stir for 2 hours at room temperature. The mixture was cooled in an ice/water bath and 2-tetrahydropyran-2-yloxyethyl bromide (1076.0 g) was dropped in as a neat oil over a period of 25 minutes. The mixture was stirred overnight at room temperature and divided into four 2-liter portions. Each portion was diluted with saturated ammonium chloride (3 L) and extracted with ether (500 mL). The combined organic layers were washed (aqueous ammonium chloride), dried, and evaporated. The resulting material was chromatographed, with hexane:dichloromethane (gradient 100:0, 0:100) as eluent, to give the nitrile as an oil (932 g); NMR: 7.47 (m,4), 7.20 (m,2), 4.57 (m,2), 4.08 (m,2), 3.85 (m,4), 3.54 (m,3), 3.37 (m,1), 2.15 (m,4), 1.77 (m,4), 1.56 (m,8).

c. 2-(3,4-Dichlorophenyl)-4-(tetrahydropyran-2-yloxy)butylamine. To a solution of the above nitrile (128.3 g) in 95% ethanol (1.1 L) and concentrated ammonium hydroxide (550 mL) was added Raney Nickel (25.0 g). The mixture was hydrogenated under a hydrogen atmosphere (3.65 bar) at room temperature for 1.5 days. The mixture was filtered through diatomaceous earth to remove the catalyst, and the resulting filtrate was evaporated. The resulting material was chromatographed, with dichloromethane:methanol (gradient 100:0, 95:5) as eluent, to give the amine (91 g) as an oil; NMR: 7.40 (s,1), 7.38 (s,1), 7.32 (d,1, J=2.1), 7.28 (d,1, J=2.0), 7.07 (dd,1, J=2.1, 4.9), 7.04 (dd,1, J=2.1, 4.9), 4.50 (m,1), 4.43 (m,1), 3.70 (m,4), 3.45 (m,2), 3.27 (m,1), 3.17 (m,1), 2.97–2.75 (m,6), 2.00 (m,2), 1.82–1.66 (m,6), 1.53 (m,8), 1.18 (broad s,4); MS: m/z=318(M+1).

d. 2-(3,4-Dichlorophenyl)-4-hydroxybutylamine. To a mechanically stirred solution of 2-(3,4-dichlorophenyl)-4-(tetrahydropyran-2-yloxy)butylamine (550 g) in methanol (3300 mL) was added in one portion 6.0N hydrochloric acid (352 mL), resulting in a slight exotherm. After being stirred for 3 hours, the reaction mixture was evaporated, and the residue was diluted with water to 3 L volume. This solution was extracted with ether (2×500 mL), made basic with sodium hydroxide pellets (100 g), and extracted with ethyl acetate (4×500 mL). The combined ethyl acetate extracts were washed (800 mL saturated sodium chloride), dried, and evaporated to give the alcohol as an amber oil (367 g) that solidified under high vacuum; NMR: 7.39 (d,1, J=8.2), 7.28 (d,1, J=2.0), 7.04 (dd,1, J=8.2, 2.0), 3.65 (m,1), 3.50 (m,1), 2.90 (m,2), 2.71 (m,1), 2.25 (m,2), 1.86 (m,2).

e. N-[2-(3,4-Dichlorophenyl)-4-hydroxybutyl]phthalimide. To a 500 mL round-bottomed flask charged with a solution of 2-(3,4-dichlorophenyl)-4- hydroxybutylamine (13.4 g) in tetrahydrofuran (250 mL) was added carboethoxyphthalimide (12.6 g/followed by triethylamine (12 mL). The reaction mixture was brought to reflux and allowed to reflux overnight (approximately 18 hours). The reaction mixture was concentrated under reduced pressure to approximately ⅓ its original volume, diluted with ethyl ether and washed twice with 0.1N hydrochloric acid (75 mL). The organic layer was washed (saturated sodium bicarbonate), dried and evaporated to afford material which was purified by chromatography, with dichloromethane:methanol (4:1) as eluent, to afford N-[2-(3,4-dichlorophenyl)-4-hydroxybutyl]phthalimide as a tacky pale yellow solid (10.2 g); NMR (DMSO): 7.85 (m,4), 7.50 (m,2), 7.20 (dd,1, J=1.9,8.3), 6.40 (broad s, ex,1), 3.80 (m,2), 3.3 (m,2), 3.15 (m,1), 1.8 (m,2); MS: m/z=364 (M+1,99%).

f. N-[2-(3,4-Dichlorophenyl)-4-oxobutyl]phthalimide. A 500 mL round-bottomed flask was charged with oxalyl chloride (2.9 mL) in dichloromethane (70 mL) and cooled to −78° C. To this solution was added dimethylsulfoxide (4.7 mL) in dichloromethane (30 mL) and the reaction mixture was stirred at this temperature for 1 hour. A precooled (0° C.) solution of N-[2-(3,4-dichlorophenyl)-4-hydroxybutyl]phthalimide (10.2 g) in dichloromethane (30 mL) was added to the above reaction mixture. After an additional 1 hour at −78° C. triethylamine (18 mL) was added and the mixture was maintained at −78° C. for 45 minutes after which it was brought to room temperature. The mixture was sequentually diluted with water (50 mL) and 1N hydrochloric acid (50 mL) and the phases were separated. The aqueous phase was extracted with dichloromethane (2×50 mL) and the combined organic extracts were washed (water, brine), dried, and filtered through a fritted glass buchner funnel containing a pad of 2 cm diatomaceous earth and 4 cm of silica gel. The filtrate was evaporated to afford the aldehyde (8.13 g) in 84% yield as an off-white solid; NMR (DMSO): 9.55 (s,1), 7.80 (m, 4), 7.60 d, 1, J=2.0), 7.50 (d,1, J=8.30), 7.25 (dd,1, J=2.1, 8.27), 3.80 (m,2), 3.65 (m,1), 3.0 (m,2); MS: m/z=362 (M+1,100%).

g. N-[4-(4-Acetamido-4-phenylpiperidino)-2-(3,4-dichlorophenyl)butyl]phthalimide. To a solution of aldehyde (8.1 g) in methanol (30 mL) was added a solution of 4-acetamido-4-phenylpiperidine (5.85 g) in methanol (75 mL) and the mixture was cooled to 0° C. To this was added acetic acid (1.8 mL) followed by a solution of sodium cyanoborohydride (1.97 g) in methanol (25 mL). The mixture was stirred at 0° C. for 2 hours and then allowed to warm to room temperature. The mixture was evaporated to approximately ⅓ its original reaction volume, diluted with dichloromethane (75 mL), water (50 mL), and saturated sodium bicarbonate (50 mL). The mixture was stirred until the suspended solids had dissolved and the layers were separated. The aqueous layer was extracted twice with dichloromethane chloride. The combined organic layers were washed (brine), dried, and filtered through a pad of 2 cm diatomaceous earth and 2 cm of silica gel in a 150 mL (6.5 cm in diameter) glass-fritted buchner funnel. The filtrate was evaporated to yield N-[4-(4-acetamido-4-phenylpiperidino)-2-(3,4-dichlorophenyl)butyl]phthalimide as an off-white foam (10.9 g); mp 83°–85° C.; NMR (d⁶-DMSO-trifluoroacetic acid): 7.80 (s,4) 7.75 (s,1), 7.53 (m,2), 7.22 (m,6), 3.83 (m,2), 3.20 (m,1), 2.60 (m,2) 2.15 (m,6), 1.85 (s,3), 1.95–1.65 (m,6); MS: m/z=564 (M+1, 86%); TLC: Rf=0.23 (20:1 dichloromethane:methanol). It is noted that this compound is also a compound of the invention.

h. 4-(4-Acetamido-4-phenylpiperidino)-2-(3,4-dichlorophenyl)butylamine. To a solution of N-[4-(4-acetamido-4-phenylpiperidino)-2-(3,4-dichlorophenyl) butyl]phthalimide (10.9 g) in ethanol (60 mL) was added hydrazine (1.2 mL) and the mixture was brought to gentle reflux. Within 15 minutes a heavy precipitate had formed and the mixture was cooled to room temperature. Water (50 mL) and dichloromethane (50 mL) were added and the mixture stirred until both the suspended solids had dissolved. Concentrated hydrochloric acid was slowly added until pH 1–2 was obtained, the layers were separated, and the aqueous layer was made basic to pH 10–11 by the addition of aqueous sodium hydroxide (1N). The basic aqueous layer was extracted twice with dichloromethane (2×75 mL) and the combined organic layers washed (brine), dried, and evaporated to afford the amine as a white foam (6.17 g); mp 56°–58° C.; NMR (DMSO-D₂O) 7.75 (broad s,1), 7.55 (m,2), 7.40–7.15 (m,5), 2.80–2.55 (m,4), 2.35–1.95 (m,6), 1.90 (s,3), 1.65 (m,1); MS: m/z=434(M+1,100%); TLC: Rf=0.17 (10:1 dichloromethane:methanol).

EXAMPLES 2–6

Using a procedure similar to that described in Example 1, except replacing 3,5-bis(trifluoromethyl)benzaldehyde with the requsite aldehyde, the following compounds of formula I wherein $Q^1$ is 4-hydroxy-4-phenylpiperidino, $Q^2$ is hydrogen, $Q^4$ is 3,4-dichlorophenyl and $Q^3$ has the indicated value were prepared.

EXAMPLE 2

$Q^3$=Benzyl; mp 76°–78° C.; NMR (DMSO-D₂O): 7.55 (2d,2), 7.77 (s,1), 7.34–7.13 (m,11), 3.72 (s,2) 2.95–2.55 (m,4), 2.35–2.05 (m,6), 1.75 (s,3), 2.0–1.6 (m, 5); MS: m/z=524(M+1,100%); TLC: Rf=0.11 (10:1 dichloromethane:methanol Analysis for $C_{30}H_{35}Cl_2N_3O.1.25\ H_2O$: Calculated: C, 65.87; H 6.91; N, 7.68; Found: C, 65.50; H, 6.52; N, 7.44.

EXAMPLE 3

$Q^3$=Phenethyl; mp 71°–73° C.; NMR (d⁶-DMSO-trifluoroacetic acid): 7.77 (s,1), 7.50 (dd,2), 7.40–7.0 (mm, 11), 2.88–2.57 (m,8), 2.28 (m,2), 2.20–1.95 (m,4), 1.95–0.170 (m,3), 1.53 (m,1); MS: m/z=538(M+1,100%). Analysis for $C_{31}H_{37}Cl_2N_3O.0.50\ H_2O$: Calculated: C, 68.00; H, 6.99; N, 7.67; Found: C, 67.86; H, 6.77; N, 7.64.

EXAMPLE 4

$Q^3$=3-Methoxybenzyl; mp 58°–60° C.; NMR: (d⁶-DMSO-trifluoroacetic acid): 7.5 (m,2), 7.40–7.10 (m,7), 6.88–6.77 (m,3), 3.70 (s,3), 2.80 (m,1), 2.75–2.55 (m,2), 2.25 (d,2), 2.20–1.97 (m,4), 1.85 (s,3), 1.97–1.55 (m, 6); MS: m/z=554(M+1,100%); TLC: Rf=0.36 (10:1 dichloromethane:methanol); Analysis for $C_{31}H_{37}Cl_2N_3O_2.0.5\ H_2O$: Calculated: C, 66.07; H, 6.80; N, 7.46; Found: C, 66.08; H, 6.66; N, 7.44.

EXAMPLE 5

$Q^3$=3,5-bis(trifluoromethyl)phenylethyl; mp 113°–115° C.; NMR (d⁶-DMSO-trifluoroacetic acid): 7.95 (s,3), 7.70 (m,2), 7.50–7.20 (m,6), 3.55–3.05 (m,3), 2.83 (m,1), 2.70–2.45 (m,4), 2.35–2.05 (broad m,4), 1.95 (s,3); MS: m/z=674(M+1,100%), FAB Exact mass for $C_{33}H_{36}Cl_2F_6N_3O(M+1)$: Calculated: 674.2140; Found: 674.2171; TLC: Rf=0.37 (10:1 dichloromethane:methanol). Analysis for $C_{33}H_{35}Cl_2F_6N_3O.2.0\ H_2O.1.5\ HCl$: Calculated: C, 51.79; H, 5.33; N, 5.49; Found: C, 51.99; H, 5.04; N, 5.68.

EXAMPLE 6

$Q^3$=2-Methoxybenyl; mp 71°–73° C.; NMR: (d$^6$-DMSO-trifluoroacetic acid): 7.55–7.45 (m,3), 7.35–7.1 (m,7), 6.95–6.80 (m,2), 3.70 (s,3), 2.60 (AB q,2), 2.85 (m,1), 2.80–2.65 (m,2), 2.25 (d,2), 2.20–2.0 (m,4), 1.85 (s,3), 1.95–1.55 (m,4); MS: m/z=554(M+1, 18%). Analysis for $C_{31}H_{37}Cl_2N_3O_2 \cdot 0.75\ H_2O$: Calculated: C, 65.54; H, 6.83; N, 7.40; Found: C, 65.46; H, 6.59; N, 7.50.

EXAMPLE 7

4-(4-Acetamido-4-phenylpiperidino)-N-benzyl-2-(3,4-dichlorophenyl)-N-[3,5-bis(trifluoromethyl)benzyl]butylamine Using a procedure similar to that described in Example 1, except replacing the (3,4-dichlorophenyl)butylamine and the 3,5-bis-(trifluoromethyl)benzaldehyde used therein with 4-(4-acetamido-4-phenylpiperidino)-2-(3,4-dichlorophenyl)-N-[3,5-bis(trifluoromethyl)benzyl]butylamine and benzaldehyde, respectively, the title compound was prepared; mp 65°–67° C.; NMR: 7.85 (s,1), 7.75 (s,1), 7.65 (s,1), 7.45 (s,1), 7.40–6.95 (broad m,10), 3.85 (d,1, J=15.9), 3.65 (d,1 J=13.6) 3.56 (d,1, J=15.9), 3.42 (d,1, J=13.6), 3.05 (m, 1), 2.75–2.40 (m,4), 2.35–2.18 (m, 2), 2.18–1.95 (m,4), 1.85 (s,3); MS: m/z=750(M+1,100%). Analysis for $C_{39}H_{39}Cl_2F_6N_3O$: Calculated: C, 61.10; H, 5.13; N, 5.48; Found: C, 61.12; H, 5.34; N, 5.65.

EXAMPLE 8

4-(4-Acetamido-4-phenylpiperidino)-2-(3,4-dichlorophenyl)-N-phenethyl-N-[3,5-bis(trifluoromethyl)benzyl]butylamine.

Using a procedure similar to that described in Example 1, except replacing the (3,4-dichlorophenyl)butylamine and the 3,5-bis(trifluoromethyl)benzaldehyde used therein with 4-(4-acetamido-4-phenylpiperidino-2-(3,4-dichlorophenyl)-N-[3,5-bis(trifluoromethyl)benzyl]butylamine and phenylacetaldehyde, respectively, the title compound was prepared; mp 55°–57° C.; partial NMR (DMSO): 7.1–6.95 (broad m,11), 3.88 (d,1), 3.65 (d,1), 3.35(d,1), 3.15(d,1), 1.85 (s,3); MS: m/z=764(M+1,100%); TLC: Rf=0.44 (10:1 dichloromethane:methanol). Analysis for $C_{40}H_{41}Cl_2F_6N_3O$: Calculated: C, 62.83; H, 5.40; N, 5.50; Found: C, 63.18; H, 5.71; N, 5.35.

EXAMPLE 9

4-(4-Acetamido-4-phenylpiperidino)-2-(3,4-dichlorophenyl)-N,N-bis(phenethyl)butylamine Using a procedure similar to that described in Example 1, except replacing the (3,4-dichlorophenyl)butylamine and the 3,5-bis(trifluoromethyl)benzaldehyde used therein with 4-(4-acetamido-4-phenylpiperidino)-2-(3,4-dichlorophenyl)-N-(phenethyl)butylamine (prepared at Example 3) and phenylacetaldehyde, respectively, the title compound was prepared; mp 60°–62° C.; NMR (d$^6$-DMSO-trifluoroacetic acid): MS: m/z=642(M+1,100%); TLC: Rf=0.76 (5:1 dichloromethane:methanol). Analysis for $C_{39}H_{45}Cl_2N_3O \cdot 0.25\ H_2O$: Calculated: C, 72.38; H, 7.09; N, 6.49; Found: C, 72.44; H, 7.07; N, 6.80.

EXAMPLE 10

4-(4-Acetamido-4-phenylpiperidino)-N-acetyl-2-(3,4-dichlorophenyl)-N-[3,5-bis(trifluoromethyl)benzyl]butylamine To a stirred solution of 4-(4-acetamido-4-phenylpiperidino)-2-(3,4-dichlorophenyl)-N-[3,5-bis(trifluoromethyl)benzyl]butylamine (0.4 g) in tetrahydrofuran (4 mL) was added acetic anhydride (0.085 mL) and diisopropylethylamine (0.32 mL). After 2 hours at room temperature 4-dimethylaminopyridine (7 mg) was added and the mixture was stirred overnight. Additional acetic anhydride (0.06 mL) was added and the reaction mixture was brought to reflux for 3 hours. The mixture was allowed to cool and diluted with aqueous hydrochloric acid (1N, 3 mL), dichloromethane (5 mL), and water (5 mL). The phases were separated and the aqueous layer was extracted with dichloromethane (2×5 mL). The combined organic phases were washed (brine), dried, and evaporated to afford crude product, which was purified by chromatography with dichloromethane:methanol (15:1) as eluent, to afford the title compound as a white solid; mp 115°–117° C.; NMR (d$^6$-DMSO-trifluoroacetic acid): 8.0–7.5 (m,5), 7.45–7.2 (m,6), 4.80–4.45 (m,2), 3.45 (m,2), 3.1 (m,4), 2.67 (m,1), 2.67 (m,2), 2.55 (s,3), 1.95 (s,3), 2.0 (broad m,5); MS: m/z=702 (M+1,100%). Analysis for $C_{34}H_{35}Cl_2F_6N_3O_2 \cdot 1.50\ H_2O$: Calculated: C, 55.97; H, 5.25; N, 5.76; Found: C, 55.91; H, 5.11; N, 5.76.

EXAMPLES 11–13

Using a procedure similar to that described in Example 10, except replacing 4-(4-acetamido-4-phenylpiperidino)-2-(3,4-dichlorophenyl)-N-[3,5-bis(trifluoromethyl)benzyl]butylamine with the required amine, the following compounds of formula I wherein $Q^1$ is 4-hydroxy-4-phenylpiperidino, $Q^2$ is acetyl, $Q^4$ is 3,4-dichlorophenyl and $Q^3$ has the indicated value were prepared.

EXAMPLE 11

$Q^3$=benzyl; mp 96°–98° C.; MS: m/z=566(M+1,100%); TLC: Rf=0.48 (10:1 dichlormethane:methanol). Analysis for $C_{32}H_{37}Cl_2N_3O_2 \cdot 0.50\ H_2O \cdot 1.0\ HCl$: Calculated: C, 62.80; H, 6.42; N, 6.87; Found: C, 63.13, H, 6.42; N, 6.60.

EXAMPLE 12

$Q^3$=3-methoxybenzyl; mp 101°–103° C.; MS: m/z=596 (M+1,100%); TLC: Rf=0.39 (10:1 dichloromethane:methanol). Analysis for $C_{33}H_{39}Cl_2N_3O_3 \cdot 1.70\ HCl$: Calculated: C, 60.18; H, 6.23; N, 6.38; Found: C, 60.04; H, 6.09; N, 6.30.

EXAMPLE 13

$Q^3$=2-methoxybenzyl; mp 64°–66° C.; partial NMR (DMSO): 7.75 (s,1), 4.40 (dd,1), 4.15 (dd,1), 3.75 (s,3), 1.95 (s,3), 1.85 (s,3); MS: m/z=596(M+1,11%); TLC: Rf=0.29 (10:1 dichloromethane:methanol). Analysis for $C_{33}H_{39}Cl_2N_3O_3 \cdot 1.0\ HCl$: Calculated: C, 62.61; H, 6.37; N, 6.64; Found: C, 62.95; H, 6.42; N, 6.46.

EXAMPLE 14

4-(4-Acetamido-4-phenylpiperidino)-2-(3,4-dichlorophenyl)-N-methyl-N-[3,5-bis(trifluoromethyl)benzyl]butylamine To a stirred solution of 4-(4-acetamido-4-phenylpiperidino)-2-(3,4-dichlorophenyl)-N-[3,5-bis(trifluoromethyl)benzyl]butylamine (0.30 g) in methanol (4 mL) was added aqueous formaldehyde (37% w/w, 0.027 mL). The mixture was cooled to 0° C. and acetic acid (0.038 mL) was added followed by a solution of sodium cyanoborohydride (43 mg) in methanol (1 mL). The reaction mixture was allowed to warm to room temperature overnight and was diluted with dichloromethane (5 mL), water (5 mL), and saturated sodium bicarbonate (mL). The phases were separated and the aqueous layer was extracted with dichloromethane (10 mL). The combined organic phases were washed (brine), dried, and evaporated, to give material which was purified by chromatography with dichloromethane:methanol (30:1) as the eluent, to give the title compound as a hemihydrate (0.175 g); mp 72°–74° C.; NMR (d$^6$-DMSO-trifluoroacetic acid): 7.7 (m,5), 7.25 (m, 6), 3.52 (d,1, J=14.4), 3.25 (d,1, J=14.4), 3.0 (m,1), 2.7–2.45 (m,4), 2.50 (s,3), 2.35–1.95 (broad m,4), 1.85 (s,3), 1.95–1.5 (broad m,4); MS: m/z=674(M+1,100%); TLC: Rf=0.55 (10:1 dichloromethane:methanol). Analysis for $C_{33}H_{35}Cl_2F_6N_3O$.0.50 $H_2O$: Calculated: C, 57.98; H, 5.31; N, 6.15; Found: C, 57.95; H, 5.24; N, 6.52.

EXAMPLE 15

4-(4-Acetamido-4-phenylpiperidino)-2-(3,4-dichlorophenyl)-N-(3-methoxybenzyl)-N-(methyl)butylamine Using a procedure similar to that described in Example 14, except replacing 4-(4-acetamido-4-phenylpiperidino)-2-(3,4-dichlorophenyl)-N-[3,5-bis(trifluoromethyl)benzyl]butylamine with 4-(4-acetamido-4-phenylpiperidino)-2-(3,4-dichlorophenyl)-N-(3-methoxybenzyl)butylamine (prepared at Example 4), the title compound was prepared; mp 59°–61° C.; NMR: 7.50 (s,1) 7.5 (m,1), 7.4–7.1 (m,6), 3.65 (s,3), 3.40 (d,1), 2.95 (m,1), 1.83 (s,3); MS: m/z=568 (M+1,100%), TLC: Rf=0.29 (10:1 dichloromethane:methanol). Analysis for $C_{32}H_{39}Cl_2N_3O_2$.0.50 $H_2O$: Calculated: C, 66.54; H, 6.98; N, 7.28; Found: C, 66.51; H, 6.82; N, 7.16.

EXAMPLE 16

4-(4-Acetamido-4-phenylpiperidino)-2-(3,4-dichlorophenyl)-N-formyl-N-[3,5-bis(trifluoromethyl)benzyl]butylamine To a 0° C. solution of formic acid (0.09 mL) in dichloromethane (3 mL) was added 1-(3-dimethylaminopropyl)-3-ethylcarbodiimide hydrochloride (0.23 g) and the mixture stirred for 15 minutes. To this mixture was added a solution of 4-(4-acetamido-4-phenylpiperidino)-2-(3,4-dichlorophenyl)-N-[3,5-bis(trifluoromethyl)benzyl]butyl amine (0.40) and N-methylmorpholine (0.13 mL) in dichloromethane (5 mL). The mixture was allowed to warm to room temperature overnight, and was diluted with 1N hydrochloric acid (5 mL), dichloromethane, and water (5 mL). The layers were separated and the the aqueous phase was extracted with dichloromethane (10 mL). The combined organic layers were washed (brine), dried, and evaporated to afford material which was purified by chromatography with dichloromethane:methanol (20:1) as eluent, to give a hydrate of the title compound (0.206 g); mp 108°–110° C.; NMR: 8.1–7.5 (m,6), 7.3 (m,6), 4.75–4.40 (m,2), 3.75–3.3 (m,4), 3.3–3.0 (m,4), 2.85 (m,1), 1.95 (s,3), 2.25–1.80 (m,4); MS: m/z=688(M+1,100%); TLC: R$_f$=0.46 (10:1 dichloromethane:methanol). Analysis for $C_{33}H_{33}Cl_2F_6N_3O_2$.1.50 $H_2O$: Calculated: C, 55.39; H, 5.07; N, 5.87; Found: C, 55.38; H, 4.77; N, 5.84.

EXAMPLES 17–20

Using a procedure similar to that described in Example 16, except replacing 4-(4-acetamido-4-phenylpiperidino)-2-(3,4-dichlorophenyl)-N-[3,5-bis(trifluoromethyl)benzyl]butylamine with the requsite amine, the following compounds of formula I wherein Q$^1$ is 4-hydroxy-4-phenylpiperidino, Q$^2$ is formyl, Q$^4$ is 3,4-dichlorophenyl and Q$^3$ has the indicated value were prepared.

EXAMPLE 17

Q$^3$=benzyl; NMR (d$^6$-DMSO-trifluoroacetic acid): 7.75 (s,1), 7.40–7.12 (m,12), 4.50–4.15 (AB q,2), 3.5–3.2 (m,4), 3.05 (m,1), 2.35–1.95 (mm,6), 1.85 (s,3), 1.88–1.55 (m,6); MS: m/z=552(M+1,100%); TLC: Rf=0.51 (10:1 dichloromethane:methanol). Analysis for $C_{31}H_{35}Cl_2N_3O_2$.0.50 $H_2O$: Calculated: C, 66.31; H, 6.46; N, 7.48; Found: C, 66.14; H, 6.43; N, 7.42.

EXAMPLE 18

Q$^3$=3-methoxybenzyl; mp 114°–116° C.; NMR: (d$^6$-DMSO-trifluoroacetic acid): 7.58 (m,2), 7.48–7.26 (mm,6), 6.95–6.75 (m,3), 4.43 (s,2), 4.15 (d,1), 3.75 (s,3), 3.55–3.25 (m,4), 3.25–2.95 (m,4), 2.90–2.55 (m,4), 1.95 (s,3), 2.25–1.85 (broad m, 4); MS: m/z=582(M+1,100%); TLC: Rf=0.29 (10:1. dichloromethane:methanol). Analysis for $C_{32}H_{37}Cl_2N_3O_3$.1.00 HCl.30 $H_2O$: Calculated: C, 59.83; H, 6.37; N, 6.54; Found: C, 59.82; H, 6.08; N, 6.56.

EXAMPLE 19

Q$^3$=2-methoxybenzyl; mp 76°–78° C.; NMR: 8.15 (s,1), 7.8 (s,1), 7.7 (s,1), 7.50 (m,2), 7.35–6.85 (m,11), 4.45–4.10 (m,2), 3.75 (2 close singlets, 3), 3.40 (m,2), 3.25 (m,1), 3.0 (m,1), 2.5 (m,2), 2.25 (d,2), 2.05 (m,4), 1.85 (s,3), 1.6 (broad m, 4); MS: m/z=582(M+1,5%); TLC: Rf=0.23 (10:1 dichloromethane:methanol). Analysis for $C_{32}H_{37}Cl_2N_3O_3$.0.50 $H_2O$: Calculated: C, 64.97; H, 6.46; N, 7.10; Found: C, 64.78; H, 6.35; N, 7.07.

EXAMPLE 20

Q$^3$=Phenethyl; mp 71°–73° C.; NMR: 7.75 (m,2), 7.55 (m,2), 7.25 (m,8), 3.55 (m,1), 3.45 (m,1), 3.10 (m,1), 2.75 (t,1), 2.60 (m,1), 2.25 (m,2), 2.1 (m,4), 1.85 (s,3), 1.75 (m,4); MS: m/z=566 (M+1,100%); TLC: Rf=0.26 (10:1 dichloromethane:methanol). Analysis for $C_{32}H_{37}Cl_2N_3O_2$.0.75 $H_2O$: Calculated: C, 66.26; H, 6.69; N, 7.24; Found: C, 66.20; H, 6.60; N, 7.49.

EXAMPLE 21

N-Acetyl-N-benzyl-2-(3,4-dichlorophenyl)-4-(4-hydroxy-4-phenylpiperidino)butylamine Acetic acid (0.123 g) was added to a solution of 4-hydroxy-4-phenylpiperidine in methanol (3 mL). After several minutes, N-acetyl-N-benzyl-4-(3,4-dichlorophenyl)-4-oxobutylamine (0.5 g) in methanol (3 mL) was added. After two minutes, sodium cyanoborohydride (0.129 g) in methanol (3 mL) was added. The reaction was quenched with acetic acid, diluted with dichloromethane, and washed with water. The organic layer was dried (Na$_2$SO$_4$) and evaporated to give a white solid, which was purified by chromatography, with methanol:diethyl ether (5:95 then 8:92) as the eluent, to give the title compound as a white solid (0.549 g); mp 57°–62° C.; MS: m/z=525(M+1); TLC: Rf=0.25 (methanol:dichloromethane, 5:95). Analysis for $C_{30}H_{34}N_2O_2Cl_2$: Calculated: C, 68.57; H, 6.52; N, 5.33; Found: C, 68.35; H, 6.55; N, 5.67.

a. N-Benzyl-2-(3,4-dichlorophenyl)-4-(tetrahydropyran-2-yloxy]butylamine. 2-(3,4-Dichlorophenyl)-4-tetrahydropyran-2-yloxy)butylamine (0.50 g) and benzaldehyde (0.185 g) were subjected to a procedure similar to that described in Example 1 subpart g. The reaction was quenched by the addition of water and sodium bicarbonate, was extracted with dichloromethane, and the resulting organic layer was dried ($Na_2SO_4$) and evaporated. The resulting material was purified by chromatography, with methanol:dichloromethane (2:98) as the eluent, to give the benzylamine; MS: m/z=410(M+1).

b. N-Acetyl-N-benzyl-2-(3,4-dichlorophenyl)-4-(tetrahydropyran-2-yl oxy)butylamine. Using a procedure similar to that described in Example 10, except replacing the N-acetyl-N-benzyl-2-(3,4-dichlorophenyl)-4-(4-hydroxy-4-phenylpiperidino)butylamine with N-benzyl-2-(3,4-dichloro-phenyl)-4-(tetrahydropyran-2-yloxy]-butylamine, the acetyl compound was prepared. The material was used in the next step without purification.

c. N-Acetyl-N-benzyl-2-(3,4-dichlorophenyl)-4-hydroxybutyl-amine. 3N HCL (12 mL) was added to N-acetyl-N-benzyl-2-(3,4-dichlorophenyl)-4-(tetrahydropyran-2-yloxy)butylamine (1.56 g) in tetrahydrofuran (12 mL). After 5 hours, the solution was neutralized with sodium hydroxide, diluted with water, and extracted with dichloromethane. The combined organic layers were dried and evaporated to give the alcohol compound (1.2 g).

d. N-Acetyl-N-benzyl-4(3,4-dichlorophenyl)-4-oxobutylamine. N-Acetyl-N-benzyl-2-(3,4-dichlorophenyl)-4-hydroxybutyl-amine (1.2 g) was oxidized using conditions similar to those described in Example 1 subpart f. to give material which was purified by chromatography, with methanol:dichloromethane (5:95) as the eluent, to give the aldehyde (0.560 g); TLC: Rf=0.38 (methanol:dichloromethane 5:95) MS: mz=364(M+1).

EXAMPLES 22–40

Using procedures similar to those described above, or described in the references cited above, the following compounds of formula I wherein $Q^4$ is dichlorophenyl, and wherein $Q^1$, $Q^2$ and $Q^3$ have the indicated values were prepared. With the exception of the compounds of Examples 29, 36, and 38, which were prepared as racemates, each of the following compounds was prepared as the (S) enantiomer at the center marked by the "*" in formula I.

EXAMPLE 22

$Q^1$=4-(2-Oxopiperidino)piperidino; $Q^2$=methyl; $Q^3$=2-methoxybenzyl; mp 96°–98° C.; MS: m/z=532(M+1); NMR: 7.70 (m, 2), 7.35 (m,3), 7.1 (m,2), 4.15–4.60 (m,2), 3.80 (r,3), 3.25–3.65 (m, 4), 2.95–3.25 (m,4), 2.50–2.90 (m,6), 2.30 (m,1), 1.90–2.20 (m,3), 1.75 (m,4). Analysis for $C_{29}H_{39}Cl_2N_3O_2$ $H_2O$: Calculated: C, 55.73; H, 6.62; N, 5.48; Found: C, 55.56; H, 6.24; N, 5.39.

EXAMPLE 23

$Q^1$=4-(2-Oxopiperidino)piperidino; $Q^2$=methyl; $Q^3$=benzyl; mp 91°–93° C.; MS: m/z=502(M+1); NMR: 7.55 (q,s,2), 7.25 (m,4), 7.15 (q,2), 4.35 (m,1), 3.5 (g,2), 3.25 (m,2), 3.1 (t,1), 3.0 (m, 1), 2.4–2.8 (broad m), 2.20 (t,2), 2.05 (m,3), 1.75–1.95 (m,3), 1.5–1.75 (m,4). Analysis for $C_{28}H_{37}Cl_2N_3O$ $H_2O$: Calculated: C, 56.34; H, 6.67; N, 5.75; Found: C, 56.12; H, 6.31; N, 5.65.

EXAMPLE 24

$Q^1$=4-(2-Oxoperhgydropyrimidin-1-yl)piperidino; $Q^2$=acetyl; $Q^3$=benzyl; mp 72°–74° C.; MS: m/z=531(M+1); NMR: 7.6 (m,2), 7.1–7.45 (m,8), 4.55 (q,1), 4.25 (m,2), 3.65 (m,1), 3.30–3.55 (m,3), 2.85–3.20 (2m,7), 2.76 (m, 1), 1.85–2.15 (m,6), 1.65–1.85 (m,1). Analysis for $C_{28}H_{36}Cl_2N_4O_2$·0.75 $H_2O$: Calculated: C, 61.70; H, 6.93; N, 10.28; Found: C, 61.41; H, 6.61; N, 10.37.

EXAMPLE 25

$Q^1$=4-(2-Oxoperhgydropyrimidin-1-yl)piperidino; $Q^2$=acetyl; $Q^3$=2-methoxybenzyl; mp 74°–76° C.; MS: m/z=561(M+1); NMR: 7.60 (m,2), 7.30 (m,2), 6.95 (m,3), 4.15–4.55 (m,2), 3.80 (s,3), 3.40–3.70 (m,3), 3.35 (m,1), 2.90–3.2 (2m,10), 2.70 (m,1), 1.90–2.15 (m,7), 1.60–1.90 (m,4). Analysis for $C_{29}H_{38}Cl_2N_4O_3$·1.00 $H_2O$: Calculated: C, 60.10; H, 6.96; N, 9.67; Found: C, 60.01; H, 6.66; N, 9.58.

EXAMPLE 26

$Q^1$=4-Acetamido-4-phenylpiperidino; $Q^2$=methyl; $Q^3$=2-methoxybenzyl; mp 75°–77° C.; MS: m/z=568(M+1); NMR: 7.7 (m,2), 7.4–7.5 (s,m,8), 7.15 (d,1), 7.05 (t,2), 4.15–4.60 (m,2), 3.82 (2S,3), 3.55–3.70 (m,3), 3.4–3.55 (m,3), 3.0–3.25 (m,3), 2.5–2.9 (m,4), 2.0–2.25 (m,4), 1.95 (s,3). High resolution mass calculated: 568.2487; Found: 568.2498.

EXAMPLE 27

$Q^1$=4-(2-Oxoperhgydropyrimidin-1-yl)piperidino; $Q^2$=hydrogen; $Q^3$=2-methoxybenzyl; mp 57°–59° C.; MS: m/z=519(M+1); NMR: 7.7 (m,2), 7.4 (m,3), 7.1 (d,1), 7.0 (t,1), 4.30 (m,1), 4.15 (rr,2), 3.8 (s,8,3), 3.5 (d,2), 3.3 (m,2), 3.1–3.25 (m,u), 2.90–3.1 (m,3), 2.6 (m,1), 2.1–2.25 (m,1), 1.90–2.1 (m, 3), 1.70–1.90 (broad m, 4). Analysis for $C_{27}H_{36}Cl_2N_4O_2$·1.00 $H_2O$: Calculated: C, 60.33; H, 7.13; N, 10.42; Found: C, 60.44; H, 6.92; N, 10.52.

EXAMPLE 28

$Q^1$=4-Acetamido-4-phenylpiperidino; $Q^2$=hydrogen; $Q^3$=2-methoxybenzyl; mp 69°–71° C.; MS: m/z=554(M+1); NMR: 7.70 (s,2), 7.35–7.50 (m,7), 7.25 (m,1), 7.15 (d,1), 7.0 (t,1), 4.15 (d,d,2), 3.85 (s,3), 3.45 (d,2), 3.30 (m,2), 3.1–3.25 (m,4), 2.70 (m,1), 2.65 (m,1), 2.0–2.25 (m,4), 1.95 (s,3). Analysis for $C_{31}H_{37}Cl_2N_3O_2$·0.75 $H_2O$: Calculated: C, 65.54; H, 6.83; N, 7.40; Found: C, 65.50; H, 6.51; N, 7.61.

EXAMPLE 29

$Q^1$=4-Acetamido-4-phenylpiperidino; $Q^2$=methylaminocarbonyl; $Q^3$=2-methoxybenzyl; mp 85°–87° C.; MS: m/z=611(M+1); NMR: 7.75 (s,1), 7.55 (d,2), 7.25 (m,8), 6.80 (m,1), 6.70 (m,2), 4.40 (d,1), 4.05 (d,1), 3.70 (s,3), 3.35 (m,4), 2.60 (d,3), 2.25 (m,2), 2.05 (m,4), 1.85 (s,3), 1.75 (m,4). Analysis for $C_{33}H_{40}Cl_2N_4O_3$·0.80 $H_2O$: Calculated: C, 63.31; H, 6.70; N, 8.95; Found: C, 63.15; H, 6.51; N, 8.79.

EXAMPLE 30

$Q^1$=4-Hydroxy-4-phenylpiperidino; $Q^2$=methyl; $Q^3$=3,5-dimethylbenzyl; mp 96°–98° C.; MS: m/z=525(M+1); NMR: 7.60 (s,1), 7.56 (s,1), 7.45 (d,2), 7.35 (t,2), 7.25 (t,2), 6.7 (s,1), 6.6 (s,2), 5.25 (broad s,1), 3.3–3.5 (m,2), 3.1–3.6 (broad m,3), 2.7–3.1 (broad m,4), 2.4–2.7 (broad m,4), 1.95–2.3 (m,12), 1.85 (m,1), 1.75 (d,2). Analysis for $C_{31}H_{38}Cl_2N_2O$: Calculated: C, 61.92; H, 6.46; N, 3.90; Found: C, 62.19; H, 6.55; N, 3.87.

EXAMPLE 31

$Q^1$=4-Hydroxy-4-phenylpiperidino; $Q^2$=acetyl; $Q^3$=3,5-dimethylbenzyl; mp 93°–95° C.; MS: m/z=553(M+1);

NMR: 7.15–7.70 (m,8), 6.85–6.95 (m,3), 3.2–3.65 (m), 3.0–3.2 (broad m,1), 2.1 (broad m, 6), 1.8–2.1 (broad m,2), 1.45–1.8 (m, 2). Analysis for $C_{32}H_{38}Cl_2N_2O_2$: Calculated: C, 64.16; H, 6.73; N, 4.68; Found: C, 63.73; H, 6.50; N, 4.62.

EXAMPLE 32

$Q^1$=4-(2-Oxoperhgydropyrimidin-1-yl)piperidino; $Q^2$=formyl; $Q^3$=2-methoxybenzyl; mp 71°–73° C.; MS: m/z=547(M+1); NMR: 8.2 (s,1), 7.9 (s,1), 7.5–7.7 (m,2), 7.1–7.4 (m), 6.85–7.1 (m), 6.3 (broad s,1), 4.2 (broad s,1), 4.1–4.35 (m,2), 3.8 (2S,3), 3.4 (m,3), 3.05 (m,5), 2.7–3.15 (broad m,1), 1.7–2.0 (m,5), 1.65 (broad m, 1).

EXAMPLE 33

$Q^1$=4-Hydroxy-4-phenylpiperidino; $Q^2$=formyl; $Q^3$=3,5-dimethylbenzyl; mp 65°–67° C.; MS: m/z=539(M+1); NMR: 8.2 (s,1), 7.9 (s,1), 7.55 (t,2), 7.45 (m,2), 7.3 (t,2), 7.2 (m,2), 6.9 (d,1), 6.8 (d,2), 4.7 (broad s,1), 4.3 (m,2), 3.2–3.6 (broad m,2), 3.0 (m,1), 2.4 (m,1), 2.25 (m,8), 2.1 (m,2), 1.6–1.90 (m,4), 1.45–1.60 (d,2). Analysis for $C_{31}H_{36}Cl_2N_2O_2$: Calculated: C, 69.01; H, 6.73; N, 5.19; Found: C, 67.96; H, 6.69; N, 5.25.

EXAMPLE 34

$Q^1$=4-Hydroxy-4-phenylpiperidino; $Q^2$=hydrogen; $Q^3$=3,5-dimethylbenzyl; mp 65°–67° C.; MS: m/z=511(M+1); NMR: 7.45–7.76 (m,3), 7.15–7.45 (m,5), 7.0 (s,2), 6.8–6.95 (m,2), 5.1 (broad s,1), 3.85 (m,2), 2.9–3.2 (m,3), 2.6–2.90 (m,5), 2.1–2.35 (m,8), 2.0 (m,1), 1.7–1.9 (m,2), 1.4–1.7 (m,2).

EXAMPLE 35

$Q^1$=4-Hydroxy-4-phenylpiperidino; $Q^2$=tert-butoxycarbonyl; $Q^3$=3,5-dimethylbenzyl; MS: m/z=611(M+1); NMR: 9.75 (broad s,1), 7.55 (m,1), 7.45 (m,3), 7.3 (t,2), 7.2 (t,2), 6.85 (s,1), 6.75 (s,2), 4.2 (m,2), 2.95–3.55 (broad m,4), 2.4–2.6 (m,1), 2.0–2.4 (m,1), 1.6–1.9 (m,4), 1.50 (m,2), 1.15–1.45 (broad s, 9). Analysis for $C_{35}H_{44}Cl_2N_2O_3.0.50 H_2O$: Calculated: C, 67.73; H, 7.31; N, 4.51; Found: C, 67.36; H, 7.02; N, 4.75.

EXAMPLE 36

$Q^1$=4-Acetamido-4-phenylpiperidino; $Q^2$=formyl; $Q^3$=phenethyl; mp 71°–73° C.; MS: m/z=566(M+1); NMR: 7.75 (m,2), 7.55 (m,2), 7.25 (m,8), 3.55 (m,1), 3.45 (m,1), 3.10 (m,1), 2.75 (t,1), 2.60 (m,1), 2.25 (m,2), 2.10 (m,4), 1.85 (s,3), 1.75 (m,4). Analysis for $C_{32}H_{37}Cl_2N_3O_2.0.75 H_2O$: Calculated: C, 66.26; H, 5.69; N, 7.24; Found: C, 66.20; H, 6.60; N, 7.49.

EXAMPLE 37

$Q^1$=4-(2-Oxopiperidino)piperidino; $Q^2$=methyl; $Q^3$=3,5-dichlorobenzyl; mp 94°–96° C.; Analysis for $C_{28}H_{37}Cl_2N_3O_3$: Calculated: C, 62.92; H, 6.98; N, 7.86; Found: C, 62.70; H, 7.05; N, 7.91.

EXAMPLE 38

$Q^1$=4-Acetamido-4-phenylpiperidino; $Q^2$=benzyl; $Q^3$=benzyl; mp 71°–73° C.; MS: m/z=614(M+1); NMR: 7.50 (broad,1), 7.0–7.40 (broad m,18), 3.50–3.65 (m,4), 3.05 (m,1), 2.60 (m,2), 2.25 (m,3), 2.05 (m,3), 1.85 (s,3), 1.75 (m,2), 1.50 (m,1). Analysis for $C_{37}H_{41}Cl_2N_3O.0.75 H_2O$: Calculated: C, 70.75; H, 6.82; N, 6.69; Found: C, 70.63; H, 6.66; N, 6.82.

EXAMPLE 39

$Q^1$=4-(2-Oxoperhydropyrimidin-1-yl)piperidino; $Q^2$ and $Q^3$ together with the nitrogen to which they are attached form a phthalimide group; mp 80°–82° C.; MS: m/z=529 (M+1); NMR: 7.88 (m,4), 7.55 (d,1, J=1.83), 7.50 (d,1 J=8.21), 7.20 (dd,1, J=8.29,1.86), 6.15 (s,1), 4.0 (m,1), 3.80 (m,2), 3.15 (m,1), 3.05 (m,4), 2.75 (m,2), 2.1 (m,2), 1.80 (broad m,6), 1.50 (m,2), 1.35 (m,2). Analysis for $C_{27}H_{30}Cl_2N_4O_3.1.00 H_2O$: Calculated: C, 59.23; H, 5.89; N, 10.23; Found: C, 59.43; H, 5.63; N, 10.30.

EXAMPLE 40

$Q^1$=4-Acetamido-4-phenylpiperidino; $Q^2$ and $Q^3$ together with the nitrogen to which they are attached form a phthalimide group; mp 89°–91° C.; MS: m/z=564(M+1,100%); NMR: 7.85 (s,4), 7.45–7.60 (s,3), 7.15–7.30 (m,5), 3.80 (m,2), 3.20 (m,1), 2.60 (m,1), 1.85 (s,3), 1.65–2.30 (m,9). Analysis for $C_{31}H_{31}Cl_2N_3O_3.0.75 H_2O$: Calculated: C, 64.41; H, 5.67; N, 7.27; Found: C, 64.48; H, 5.68; N, 7.30.

FORMULAE

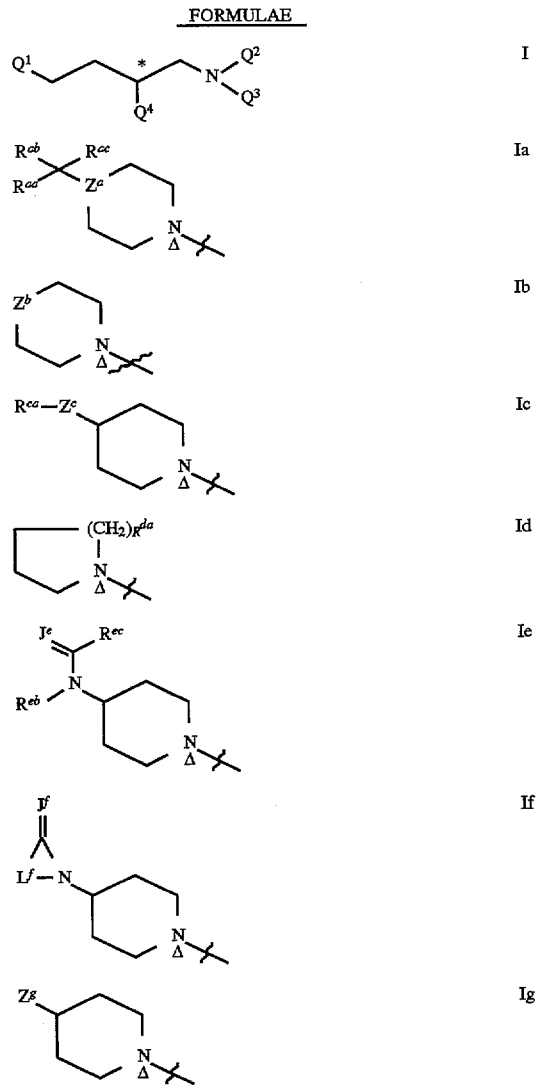

-continued
FORMULAE
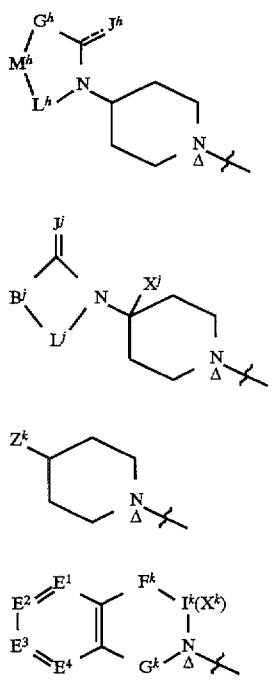
Ih
Ij
Ik
Il
-continued
FORMULAE
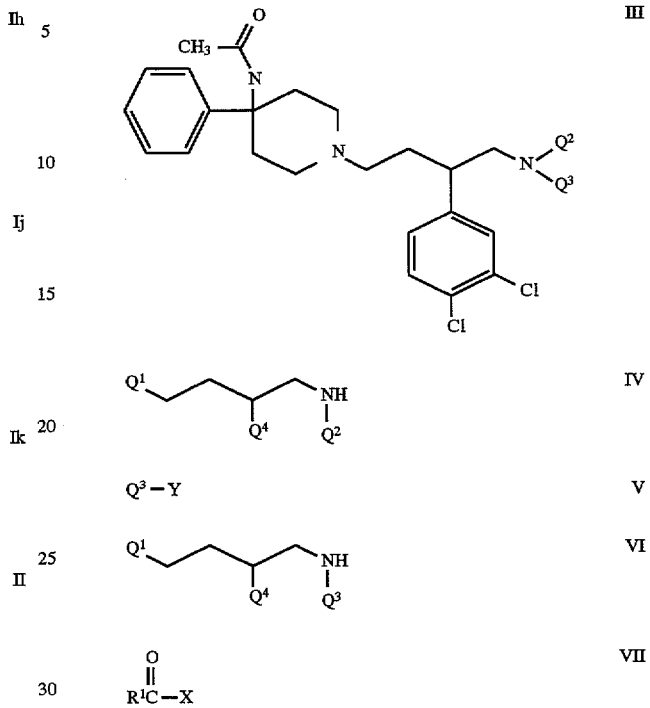
III
IV
V
VI
VII
Scheme I
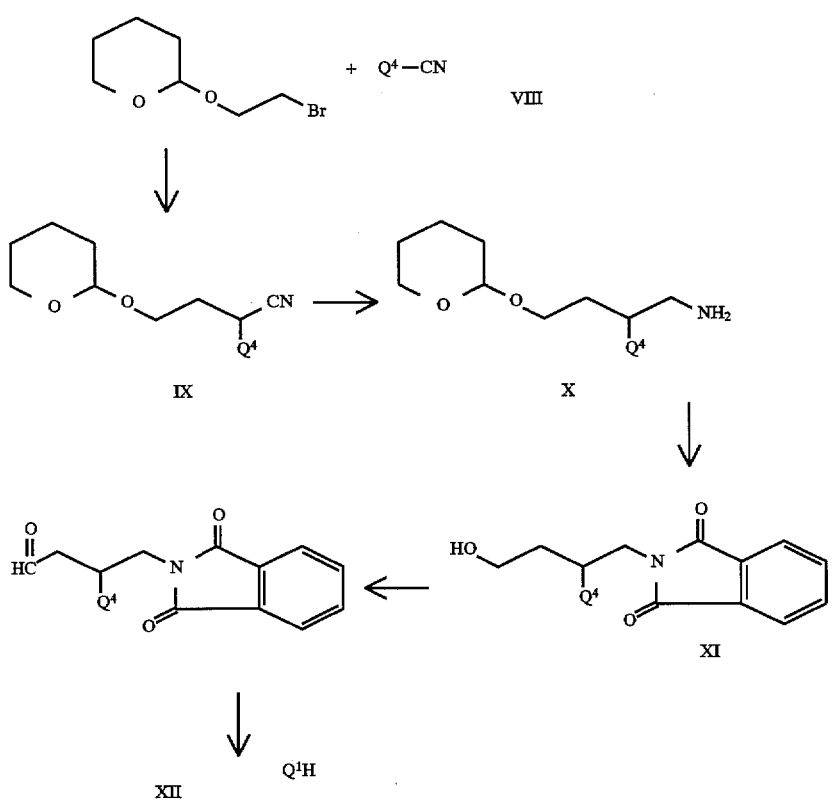

-continued
Scheme I

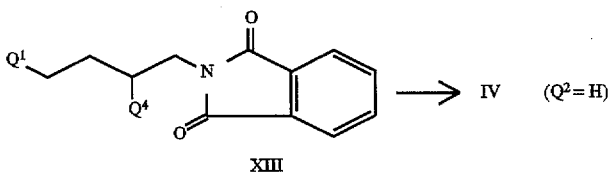

What is claimed is:

1. A compound of formula I:

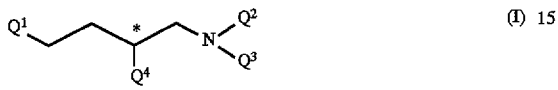

wherein $Q^1$ is a radical selected from the group of radicals of formulae Ib and Ic:

wherein for a radical of formula Ib, $Z^b$ is a disubstituted methylene group $R^{bb}(CH_2)_p$—C—$R^{bc}$ in which $R^{bb}$ is Ar or Het; p is the integer 0 or 1; and $R^{bc}$ is hydrogen, hydroxy, (1–4C)alkoxy, (1–4C) alkanoyloxy, COOR$^{bd}$ (wherein R$^{bd}$ is hydrogen or (1–3C)alkyl), cyano, NR$^{be}$R$^{bf}$ or SR$^{bg}$ in which R$^{be}$ and R$^{bf}$ are independently hydrogen, (1–4C)alkyl, (1–4C)hydroxyalkyl or (1–4C)alkanoyl, or the radical NR$^{be}$R$^{bf}$ is pyrrolidino, piperidino or morpholino; and R$^{bg}$ is hydrogen or (1–4C)alkyl; or R$^{bc}$ forms a double bond with the carbon atom to which it is bonded and with the adjacent carbon atom in the piperidine ring;

for a radical of formula Ic, R$^{ca}$ is Ar or Het; and $Z^c$ is oxo, thio, sulfinyl, sulfonyl or imino of formula —NR$^{cb}$— in which R$^{cb}$ is (1–3C)alkyl or R$^{cc}$R$^{cd}$N—(CH$_2$)$_q$— in which q is the integer 2 or 3 and in which R$^{cc}$ and R$^{cd}$ are independently hydrogen or (1–3C)alkyl or the radical R$^{cc}$R$^{cb}$N is pyrrolidino, piperidino or morpholino;

for a radical $Q^1$, Ar is a phenyl radical or an ortho-fused bicyclic carbocyclic radical of nine of ten ring atoms in which at least one ring is aromatic, which radical Ar may be unsubstituted or may bear one or more substituents selected from halo, cyano, trifluoromethyl, (1–4C)alkyl, (1–4C)alkoxy, methylenedioxy, hydroxy, mercapto, —S(O)$_n$R$^{xa}$, (1–5C)alkanoyl, (1–5C)alkanoyloxy, nitro, NR$^{xb}$R$^{xc}$, NR$^{xd}$R$^{xe}$, C(=NR$^{xf}$)NR$^{xg}$R$^{xh}$, CONR$^{xb}$R$^{xc}$ and COOR$^{xj}$ wherein n is the integer 0, 1, or 2; R$^{xa}$ is (1–6C)alkyl, (3–6C)cycloalkyl or phenyl (which phenyl may bear a halo, trifluoromethyl, (1–3C)alkyl or (1–3C)alkoxy substituent); the radical NR$^{xb}$R$^{xc}$ contains zero to seven carbons and each of R$^{xb}$ and R$^{xc}$ is independently hydrogen, (1–5C)alkyl or (3–6C)cycloalkyl, or the radical NR$^{xb}$R$^{xc}$ is pyrrolidino, piperidino, morpholino, thiomorpholine (or its S-oxide) or piperazinyl (which piperazinyl may bear a (1–3C)alkyl substituent at the 4-position); and wherein R$^{xd}$ is hydrogen or (1–4C) alkyl and R$^{xe}$ is (1–5C)alkanoyl, benzoyl; or a group of formula C(=J$^x$)NR$^{xg}$R$^{xh}$ in which J$^x$ is oxygen, sulfur, NR$^{xf}$ or CHR$^{xi}$; R$^{xf}$ is hydrogen, (1–5C)alkyl or together with R$^{xg}$ forms an ethylene or trimethylene diradical, the radical NR$^{xg}$R$^{xh}$ contains zero to 7 carbons and each of R$^{xg}$ and R$^{xh}$ is independently hydrogen, (1–5C)alkyl or (3–6C)cycloalkyl, or the radical NR$^{xg}$R$^{xh}$ is pyrrolidino, piperidino, morpholino, thiomorpholino (or its S-oxide) or piperazinyl (which piperazinyl may bear a (1–3C)alkyl substituent at the 4-position); or R$^{xg}$ together with R$^{xf}$ forms an ethylene or trimethylene diradical and R$^{xh}$ is hydrogen or (1–5C)alkyl; R$^{xi}$ is cyano, nitro, (1–5C)alkylsulfonyl or phenylsulfonyl; and R$^{xj}$ is hydrogen, (1–5C)alkyl or benzyl; and Het is a radical (or stable N-oxide thereof) attached via a ring carbon of a monocyclic aromatic ring containing five or six ring atoms consisting of carbon and one to four heteroatoms selected from oxygen, sulfur and nitrogen, or an ortho-fused bicyclic heterocycle derived therefrom by fusing a propenylene, trimethylene, tetramethylene or benz-diradical, which radical Het may be unsubstituted or may be substituted on carbon by one or more of the substituents defined above for Ar and may be substituted on nitrogen by (1–3C)alkyl;

$Q^2$ is hydrogen, (1–3C)alkyl, phenyl(1–3C)alkyl, —C(=O)R$^2$, or —C(=O)NR$^3$R$^4$, wherein a phenyl ring may bear one or two substituents independently selected from halo, trifluoromethyl, hydroxy, (1–3C)alkoxy, (1–3C)alkyl and methylenedioxy;

$Q^3$ is phenyl(1–3C)alkyl, wherein the phenyl ring may bear one or two substituents independently selected from halo, trifluoromethyl, hydroxy, (1–3C)alkoxy, (1–3C)alkyl and methylenedioxy; or $Q^2$ and $Q^3$ together with the nitrogen to which they are attached form a phthalimide group;

$Q^4$ is phenyl which may bear one or two substituents independently selected from halo, trifluoromethyl, hydroxy, (1–3C)alkoxy, (1–3C)alkyl and methylenedioxy; or $Q^4$ is thienyl, imidazolyl, benzo[b]thiophenyl or naphthyl any of which may bear a halo substituent; or $Q^4$ is biphenylyl; or $Q^4$ is carbon-linked indolyl which may bear a benzyl substituent at the 1-position;

$R^2$ is hydrogen (1–6C)alkyl, or (1–6C)alkoxy; and $R^3$ and $R^4$ are independently hydrogen or (1–3C)alkyl;

or the N-oxide of a piperidino nitrogen in $Q^1$ indicated by Δ in formulae Ib and Ic;

or a pharmaceutically acceptable salt thereof;

or a quaternary ammonium salt thereof in which the piperidino nitrogen in $Q^1$ indicated by Δ in formulae Ib and Ic is a quadricovalent ammonium nitrogen wherein the fourth radical on the nitrogen $R^1$ is (1–4C)alkyl or benzyl and the associated counterion A is a pharmaceutically acceptable anion.

2. A compound as claimed in claim 1, wherein: Ar is phenyl which may be unsubstituted or may bear a chloro, methyl, methoxy, hydroxy or methylsulfinyl substituent; Het is furyl, thienyl, 2-imidazolyl, 1,3,4-oxadiazol-2-yl, pyridyl or pyrimidinyl which ring may be unsubstituted or may bear a chloro, methyl, methoxy, hydroxy, methylsulfinyl, methoxycarbonyl or ethoxycarbonyl substituent; aryl is phenyl; heteroaryl is furyl, pyridyl or pyrimidinyl; halo is chloro or bromo; (1–3C)alkyl is methyl, ethyl, propyl or isopropyl; (1–4C)alkyl is methyl, ethyl, propyl, isopropyl, butyl, isobutyl or t-butyl; (1–5C)alkyl is methyl, ethyl, propyl, isopropyl, butyl, isobutyl, t-butyl, pentyl or isopentyl; (1–6C)alkyl is methyl, ethyl, propyl, isopropyl, butyl, isobutyl, t-butyl, pentyl, isopentyl, hexyl or isohexyl; (1–8C)alkyl is methyl, ethyl, propyl, isopropyl, isopentyl, 1-ethylpropyl, hexyl, isohexyl, 1-propylbutyl, or octyl; (3–6C)cycloalkyl is cyclopropyl, cyclopentyl or cyclohexyl; (3–7C)cycloalkyl is cyclopropyl, cyclopentyl, cyclohexyl or cycloheptyl; (3–8C)cycloalkyl is cyclopropyl, cyclopentyl, cyclohexyl, cycloheptyl or cyclooctyl; (3–6C)alkenyl is allyl, 2-butenyl or 3-methyl-2-butenyl; (1–4C)alkanoyl is formyl, acetyl, propionyl, butyryl or isobutyryl; and (1–5C) alkanoyl is formyl, acetyl, propionyl, butyryl, isobutyryl, valeryl, isovaleryl or pivaloyl;

or the N-oxide of a piperidino nitrogen in $Q^1$ indicated by $\Delta$ in formulae Ib and Ic;

or a pharmaceutically acceptable salt thereof;

or a quaternary ammonium salt thereof in which the piperidino nitrogen in $Q^1$ indicated by $\Delta$ in formulae Ib and Ic is a quadricovalent ammonium nitrogen wherein the fourth radical on the nitrogen $R^1$ is (1–4C)alkyl or benzyl and the associated counterion A is a pharmaceutically acceptable anion.

3. A compound as claimed in claim 1 wherein Ar is phenyl which may be unsubstituted or may bear a methoxy, hydroxy or methylsulfinyl substituent; Het is pyridyl or pyrimidinyl which ring may be unsubstituted or may bear a methoxy, hydroxy or methylsulfinyl substituent; heteroaryl is pyridyl; halo is chloro; (1–3C)alkyl is methyl; (1–4C)alkyl is methyl or ethyl; (1–5C)alkyl is methyl, ethyl, propyl or isopropyl; (1–6C)alkyl is methyl, ethyl, propyl, isopropyl, butyl, isobutyl or t-butyl; (1–8C)alkyl is methyl, ethyl, propyl, isopropyl, 1-ethylpropyl or 1-propylbutyl; (3–6C)cylcoalkyl is cyclopropyl or cyclopentyl; (3–7C)cycloalkyl is cyclopropyl or cyclopentyl; (3–8C)cycloalkyl is cyclopropyl, cyclopentyl, cyclohexyl or cycloheptyl; (3–6C)alkenyl is allyl; (1–4C)alkanoyl is formyl or acetyl; and (1–5C) alkanoyl is formyl, acetyl, propionyl, butyryl or isobutyryl;

or the N-oxide of a piperidino nitrogen in $Q^1$ indicated by $\Delta$ in formulae Ib and Ic;

or a pharmaceutically acceptable salt thereof;

or a quaternary ammonium salt thereof in which the piperidino nitrogen in $Q^1$ indicated by $\Delta$ in formulae Ib and Ic is a quadricovalent ammonium nitrogen wherein the fourth radical on the nitrogen $R^1$ is (1–4C)alkyl or benzyl and the associated counterion A is a pharmaceutically acceptable anion.

4. A compound as claimed in claim 1 wherein $Q^1$ is 4-acetamido-4-phenylpiperidino, 4-(2-methylsulfinylphenyl)piperidino, 4-(2-oxopiperidino) piperidino, or 4-(2-oxoperhydropyrimidin-1-yl)piperidino; $Q^2$ is hydrogen, benzyl, formyl, phenethyl, N-methylaminocarbonyl, acetyl, or methyl; $Q^3$ is benzyl, phenethyl, 3,5-bis(trifluoromethyl)benzyl, 3,5-bis (trifluoromethyl)phenethyl, 3-methoxybenzyl or 2-methoxybenzyl; and $Q^4$ is 3,4-dichlorophenyl, or 3,4-methylenedioxyphenyl;

or the N-oxide of a piperidino nitrogen in $Q^1$ indicated by $\Delta$ in formulae Ib or Ic;

or a pharmaceutically acceptable salt thereof;

or a quaternary ammonium salt thereof in which the piperidino nitrogen in $Q^1$ indicated by $\Delta$ in formulae Ib and Ic is a quadricovalent ammonium nitrogen wherein the fourth radical on the nitrogen $R^1$ is (1–4C)alkyl or benzyl and the associated counterion A is a pharmaceutically acceptable anion.

5. A compound as claimed in claim 1 wherein $Q^1$ is 4-acetamido-4-phenylpiperidino; and $Q^3$ is 2-methoxybenzyl;

or the N-oxide of a piperidino nitrogen in $Q^1$ indicated by $\Delta$ in formulae Ib and Ic;

or a pharmaceutically acceptable salt thereof;

or a quaternary ammonium salt thereof in which the piperidino nitrogen in $Q^1$ indicated by $\Delta$ in formulae Ib and Ic is a quadricovalent ammonium nitrogen wherein the fourth radical on the nitrogen $R^1$ is (1–4C)alkyl or benzyl and the associated counterion A is a pharmaceutically acceptable anion.

6. A compound as claimed in claim 1 wherein $Q^1$ is 4-acetamido-4-phenylpiperidino; and $Q^4$ is 3,4-dichlorophenyl;

or the N-oxide of a piperidino nitrogen in $Q^1$ indicated by $\Delta$ in formulae Ib and Ic;

or a pharmaceutically acceptable salt thereof;

or a quaternary ammonium salt thereof in which the piperidino nitrogen in $Q^1$ indicated by $\Delta$ in formulae Ib and Ic is a quadricovalent ammonium nitrogen wherein the fourth radical on the nitrogen $R^1$ is (1–4C)alkyl or benzyl and the associated counterion A is a pharmaceutically acceptable anion.

7. A compound as claimed in claim 6 wherein $Q^2$ is hydrogen or methyl;

or the N-oxide of a piperidino nitrogen in $Q^1$ indicated by $\Delta$ in formulae Ib and Ic;

or a pharmaceutically acceptable salt thereof;

or a quaternary ammonium salt thereof in which the piperidino nitrogen in $Q^1$ indicated by $\Delta$ in formulae Ib and Ic is a quadricovalent ammonium nitrogen wherein the fourth radical on the nitrogen $R^1$ is (1–4C)alkyl or benzyl and the associated counterion A is a pharmaceutically acceptable anion.

8. A pharmaceutical composition comprising a compound of formula I as defined in claim 11;

or the N-oxide of a piperidino nitrogen in $Q^1$ indicated by $\Delta$ in formulae Ib and Ic;

or a pharmaceutically acceptable salt thereof;

or a quaternary ammonium salt thereof in which the piperidino nitrogen in $Q^1$ indicated by $\Delta$ in formulae Ib and Ic is a quadricovalent ammonium nitrogen wherein the fourth radical on the nitrogen $R^1$ is (1–4C)alkyl or benzyl and the associated counterion A is a pharmaceutically acceptable anion; and a pharmaceutically acceptable diluent or carrier.

9. A method of treating a disease in a human or other mammal in need thereof, in which NKA is implicated and antagonism of its action is desired, comprising: administering an effective amount of a compound of formula I, as defined in claim 1;

or the N-oxide of a piperidino nitrogen indicated by Δ;

or a pharmaceutically acceptable salt thereof;

or a quaternary ammonium salt thereof in which the piperidino nitrogen indicated by Δ is a quadricovalent ammonium nitrogen wherein the fourth radical on the nitrogen $R^1$ is (1–4C)alkyl or benzyl and the associated counterion A is a pharmaceutically acceptable anion.

10. A method of treating a disease as described in claim 9, wherein the disease is asthma.

* * * * *